United States Patent
Matsuoka

(10) Patent No.: US 12,146,997 B2
(45) Date of Patent: Nov. 19, 2024

(54) RADIATION DETECTOR COMPRISING FIBER OPTIC PLATES AND IMAGE SENSORS, RADIATION DETECTOR MANUFACTURING METHOD, AND IMAGE PROCESSING METHOD

(71) Applicant: HAMAMATSU PHOTONICS K.K., Hamamatsu (JP)

(72) Inventor: Kenta Matsuoka, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 169 days.

(21) Appl. No.: 17/971,965

(22) Filed: Oct. 24, 2022

(65) Prior Publication Data
US 2023/0038637 A1 Feb. 9, 2023

Related U.S. Application Data

(63) Continuation of application No. 17/048,864, filed as application No. PCT/JP2019/015654 on Apr. 10, 2019, now Pat. No. 11,531,123.

(30) Foreign Application Priority Data

Apr. 24, 2018 (JP) ................. 2018-083133

(51) Int. Cl.
*A61B 6/00* (2024.01)
*A61B 6/42* (2024.01)
(Continued)

(52) U.S. Cl.
CPC ........ *G01T 1/20185* (2020.05); *A61B 6/4233* (2013.01); *A61B 6/425* (2013.01);
(Continued)

(58) Field of Classification Search
CPC ........... A61B 6/032; A61B 6/037; A61B 6/42; A61B 6/4208; A61B 6/4233;
(Continued)

(56) References Cited

U.S. PATENT DOCUMENTS

| 5,059,800 A | 10/1991 | Cueman et al. |
| 5,550,380 A | 8/1996 | Sugawara et al. |

(Continued)

FOREIGN PATENT DOCUMENTS

| EP | 0373717 A1 | 6/1990 |
| JP | H8-211155 A | 8/1996 |

(Continued)

OTHER PUBLICATIONS

International Preliminary Report on Patentability mailed Nov. 5, 2020 for PCT/JP2019/015654.

*Primary Examiner* — Allen C. Ho
(74) *Attorney, Agent, or Firm* — Faegre Drinker Biddle & Reath LLP

(57) ABSTRACT

A radiation detector includes a wiring board, a first image sensor, a second image sensor, a first fiber optic plate, a second fiber optic plate, and a scintillator layer. The first fiber optic plate can guide light between a first light entering region and a first light exiting region. The second fiber optic plate can guide light between a second light entering region and a second light exiting region. One side of the first light entering region and one side of the second light entering region are in contact with each other. The first light exiting region is positioned on a first light receiving region. The second light exiting region is positioned on a second light receiving region. One side surface of a first side surface and one side surface of a second side surface exhibit shapes along each other and in contact with each other.

16 Claims, 14 Drawing Sheets

(51) Int. Cl.
*A61B 6/51* (2024.01)
*G01T 1/20* (2006.01)

(52) U.S. Cl.
CPC ............. *A61B 6/4266* (2013.01); *A61B 6/51* (2024.01); *A61B 6/512* (2024.01); *G01T 1/2002* (2013.01); *G01T 1/2006* (2013.01); *G01T 1/201* (2013.01); *G01T 1/2018* (2013.01); *G01T 1/20182* (2020.05); *G01T 1/20187* (2020.05); *G01T 1/20188* (2020.05)

(58) Field of Classification Search
CPC ..... A61B 6/4241; A61B 6/425; A61B 6/4258; A61B 6/4266; A61B 6/4275; A61B 6/4283; A61B 6/51; A61B 6/512; G01T 1/20; G01T 1/2002; G01T 1/2006; G01T 1/201; G01T 1/2018; G01T 1/20182; G01T 1/20183; G01T 1/20184; G01T 1/20185; G01T 1/20186; G01T 1/20187; G01T 1/20188
USPC .............................. 250/370.09; 378/19, 98.8
See application file for complete search history.

(56) References Cited

U.S. PATENT DOCUMENTS

| | | | |
|---|---|---|---|
| 5,844,243 A | 12/1998 | Lee et al. | |
| 5,909,029 A * | 6/1999 | Tonami | G01T 1/20185 250/363.04 |
| 6,031,892 A | 2/2000 | Karellas | |
| 6,042,267 A | 3/2000 | Muraki et al. | |
| 6,285,739 B1 | 9/2001 | Rudin et al. | |
| 6,448,544 B1 | 9/2002 | Stanton et al. | |
| 6,479,827 B1 | 11/2002 | Hamamoto et al. | |
| 6,559,452 B1 * | 5/2003 | Tashiro | G01T 1/2928 250/366 |
| 6,635,877 B2 * | 10/2003 | Kusuyama | G01T 1/2002 250/361 R |
| 6,671,347 B2 | 12/2003 | Tashiro et al. | |
| 6,731,720 B2 | 5/2004 | Matsuura | |
| 6,781,131 B2 * | 8/2004 | Kusuyama | G01T 1/20185 250/368 |
| 6,800,836 B2 * | 10/2004 | Hamamoto | H04N 5/32 348/E3.032 |
| 6,800,857 B2 * | 10/2004 | Kajiwara | A61B 6/4216 250/370.11 |
| 6,895,077 B2 | 5/2005 | Karellas et al. | |
| 6,906,332 B2 | 6/2005 | Tashiro et al. | |
| 6,921,909 B2 | 7/2005 | Nagarkar et al. | |
| 6,928,218 B2 | 8/2005 | Nakata et al. | |
| 7,067,814 B2 * | 6/2006 | Ooi | G01T 1/1644 250/368 |
| 7,071,980 B2 | 7/2006 | Yuki et al. | |
| 7,091,492 B2 | 8/2006 | Moonen | |
| 7,138,637 B2 | 11/2006 | Miyaguchi | |
| 7,247,861 B2 | 7/2007 | Suzuki et al. | |
| 7,262,399 B2 | 8/2007 | Hayashi et al. | |
| 7,285,786 B2 | 10/2007 | Sims et al. | |
| 7,548,608 B2 | 6/2009 | Hörnig | |
| 7,573,035 B2 * | 8/2009 | Levene | G01T 1/2985 250/361 R |
| 7,608,834 B2 | 10/2009 | Boucly et al. | |
| 7,626,176 B2 | 12/2009 | Zeitler et al. | |
| 7,684,545 B2 | 3/2010 | Damento et al. | |
| 8,399,841 B2 | 3/2013 | Hansen et al. | |
| 9,136,029 B2 | 9/2015 | Toyama et al. | |
| 9,588,235 B2 | 3/2017 | Weisfield et al. | |
| 9,658,342 B2 | 5/2017 | van Arendonk et al. | |
| 9,696,435 B2 | 7/2017 | Gubbens et al. | |
| 9,698,193 B1 | 7/2017 | Karim et al. | |
| 9,702,986 B2 | 7/2017 | Peters et al. | |
| 9,743,893 B2 | 8/2017 | Inglese et al. | |
| 9,772,409 B2 | 9/2017 | Granfors et al. | |
| 9,835,735 B2 | 12/2017 | Preston | |
| 10,031,243 B2 | 7/2018 | Yamakawa et al. | |
| 10,039,441 B2 | 8/2018 | Inglese et al. | |
| 10,130,317 B2 | 11/2018 | Miller | |
| 10,168,288 B2 | 1/2019 | Bueno et al. | |
| 10,185,041 B2 | 1/2019 | Zyazin | |
| 10,213,180 B2 | 2/2019 | Kravis et al. | |
| 10,274,610 B2 * | 4/2019 | Nelson | G01T 1/2002 |
| 10,299,741 B2 | 5/2019 | Kravis et al. | |
| 10,299,742 B2 | 5/2019 | Kravis et al. | |
| 10,408,950 B2 | 9/2019 | Matsuoka | |
| 10,448,908 B2 | 10/2019 | Sasaki et al. | |
| 10,456,098 B2 | 10/2019 | van Arendonk | |
| 10,670,741 B2 | 6/2020 | Gillissen et al. | |
| 10,682,116 B2 | 6/2020 | Mollov et al. | |
| 10,775,517 B2 * | 9/2020 | Maolinbay | G01T 1/20182 |
| 10,823,858 B2 | 11/2020 | Liu et al. | |
| 10,971,541 B2 | 4/2021 | Colbeth et al. | |
| 11,103,207 B1 | 8/2021 | Singh et al. | |
| 11,129,580 B2 * | 9/2021 | Miyaguchi | A61B 6/00 |
| 11,156,727 B2 | 10/2021 | Shedlock et al. | |
| 11,237,281 B2 * | 2/2022 | Zhan | G01T 1/20184 |
| 11,313,980 B2 | 4/2022 | Nishihara et al. | |
| 11,531,123 B2 * | 12/2022 | Matsuoka | G01T 1/20182 |
| 11,576,632 B2 * | 2/2023 | Miyaguchi | A61B 5/0088 |
| 2001/0054694 A1 | 12/2001 | Kusuyama et al. | |
| 2008/0277588 A1 | 11/2008 | Zeitler et al. | |

FOREIGN PATENT DOCUMENTS

| | | |
|---|---|---|
| JP | H11-505142 A | 5/1999 |
| JP | 2000-304864 A | 11/2000 |
| JP | 2001-078099 A | 3/2001 |
| JP | 2002-139569 A | 5/2002 |
| JP | 2003-302538 A | 10/2003 |
| WO | WO 96/035372 A2 | 11/1996 |
| WO | WO 2017/048852 A1 | 3/2017 |

* cited by examiner

*Fig.4*
(a)
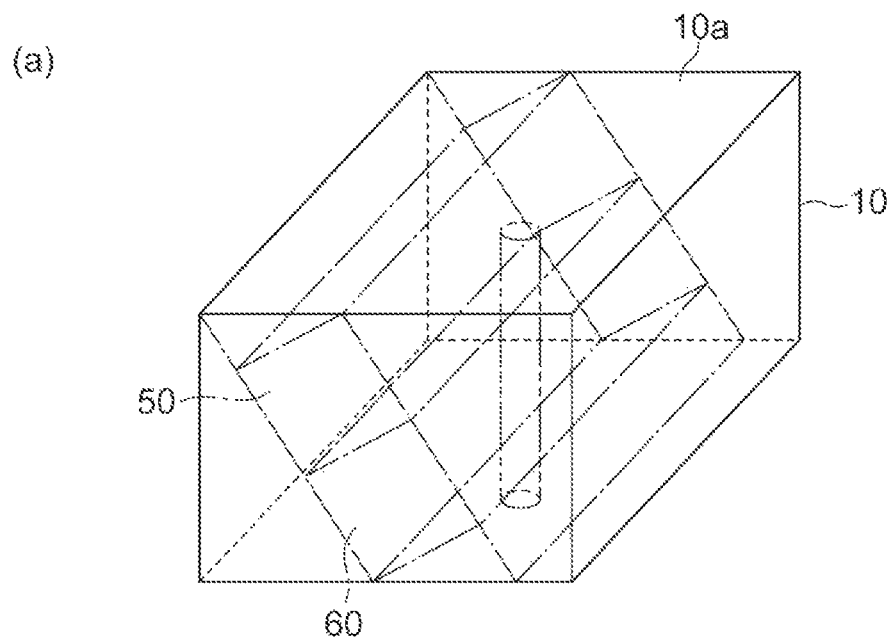
(b)
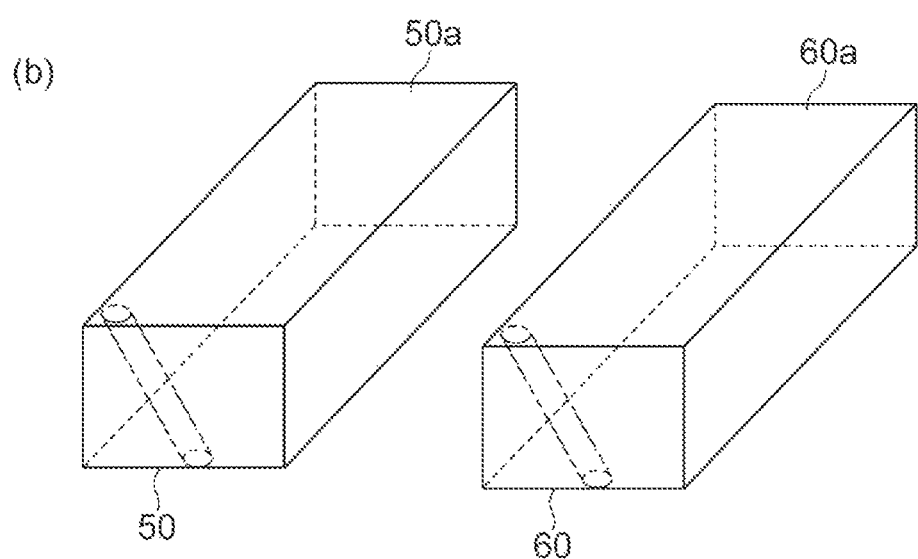

Fig.5
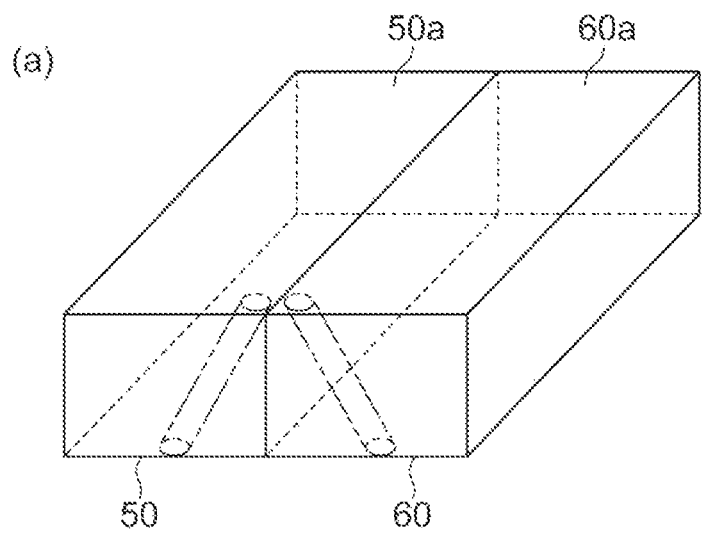
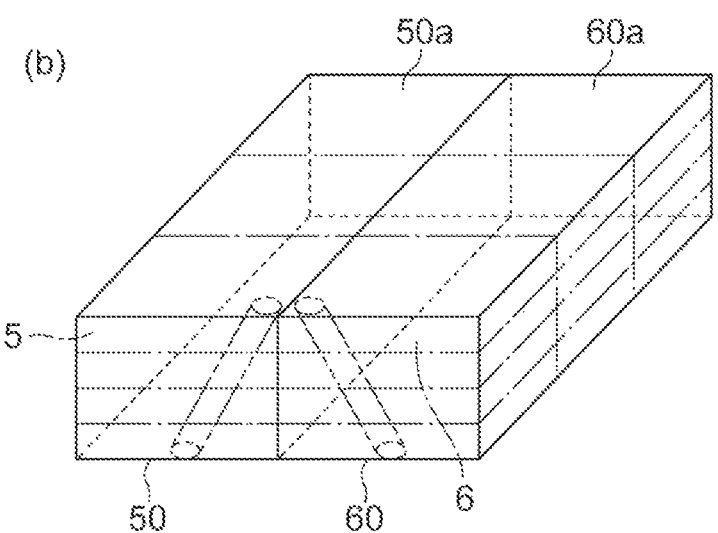
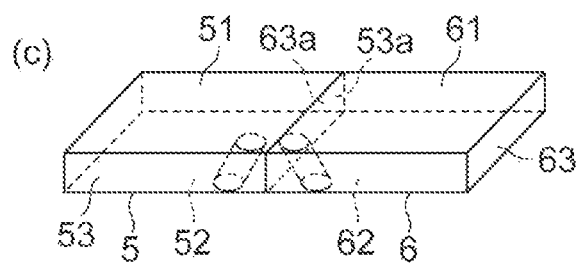

Fig.12
(a)
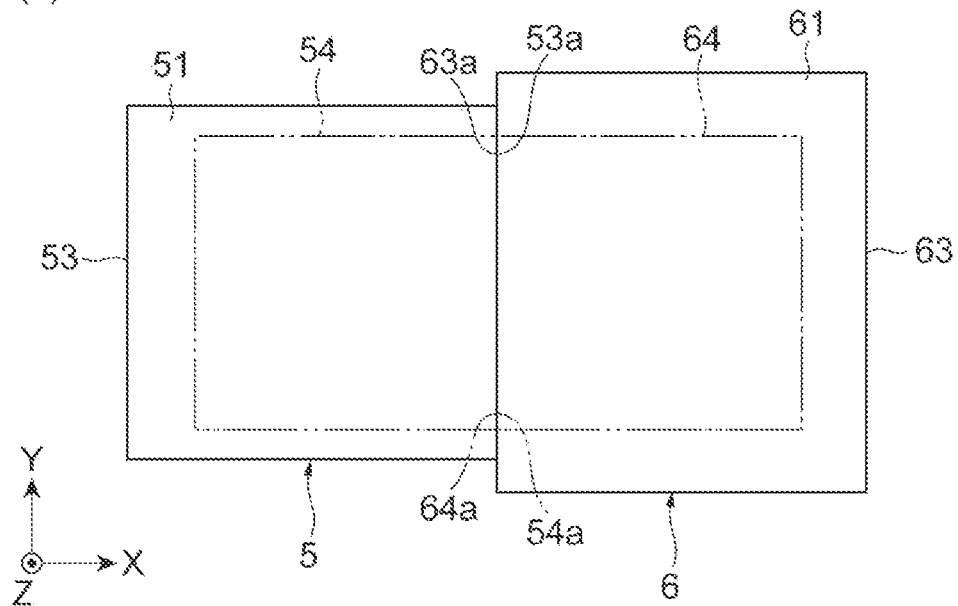
(b)
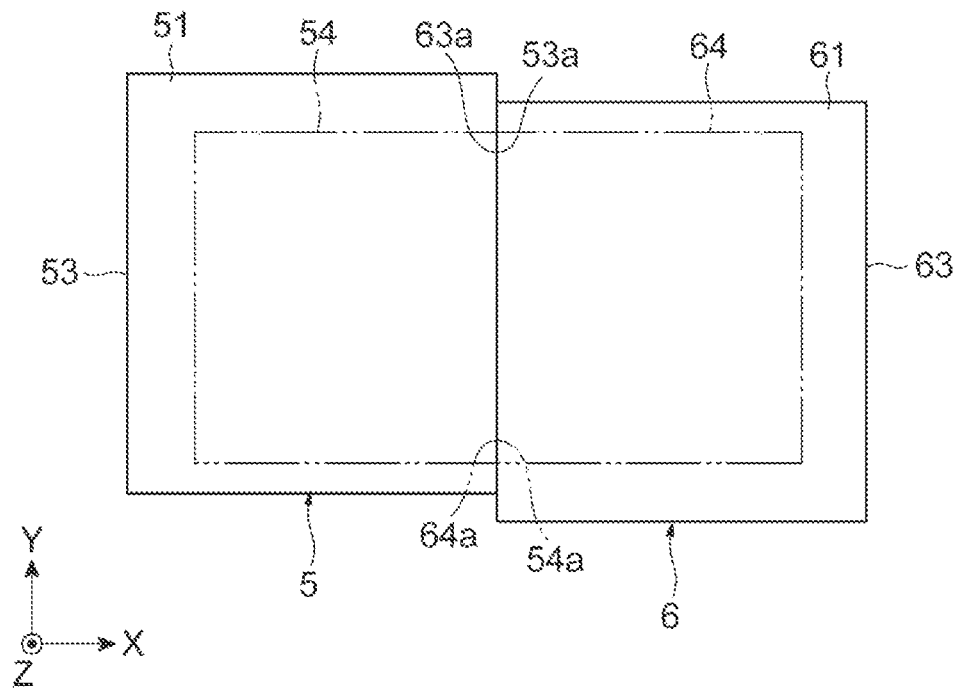

RADIATION DETECTOR COMPRISING FIBER OPTIC PLATES AND IMAGE SENSORS, RADIATION DETECTOR MANUFACTURING METHOD, AND IMAGE PROCESSING METHOD

TECHNICAL FIELD

The present disclosure relates to a radiation detector, a radiation detector manufacturing method, and an image processing method.

BACKGROUND ART

For example, a radiation detector described below may be used in order to acquire an intraoral X-ray transmission image over an extended range. That is, a radiation detector including a wiring board, a plurality of image sensors mounted on the wiring board, a plurality of fiber optic plates respectively fixed on the plurality of image sensors, and a scintillator layer provided on the plurality of fiber optic plates may be used. Regarding such a radiation detector, Patent Literature 1 describes an X-ray image sensor in which fiber optic plates adjacent to each other are brought into contact with each other in a corner part on a light entering surface side.

CITATION LIST

Patent Literature

Patent Literature 1: Japanese Unexamined Patent Publication No. H8-211155

SUMMARY OF INVENTION

Technical Problem

However, in the X-ray image sensor described in Patent Literature 1, there is concern that a positional deviation may be likely to occur between a light entering surface of one fiber optic plate and a light entering surface of the other fiber optic plate, and thus an X-ray transmission image may not be able to be accurately acquired due to the positional deviation therebetween.

An object of the present disclosure is to provide a radiation detector, a radiation detector manufacturing method, and an image processing method, in which a radiographic image can be accurately obtained over an extended range.

Solution to Problem

According to an aspect of the present disclosure, there is provided a radiation detector including a wiring board, a first image sensor and a second image sensor adjacent to each other on the wiring board, a first fiber optic plate and a second fiber optic plate adjacent to each other on the first image sensor and the second image sensor, and a scintillator layer provided on the first fiber optic plate and the second fiber optic plate. The first fiber optic plate has a first light entering surface, a first light exiting surface, and a first side surface connecting the first light entering surface and the first light exiting surface and is capable of guiding light between a first light entering region of the first light entering surface and a first light exiting region of the first light exiting surface. The second fiber optic plate has a second light entering surface, a second light exiting surface, and a second side surface connecting the second light entering surface and the second light exiting surface and is capable of guiding light between a second light entering region of the second light entering surface and a second light exiting region of the second light exiting surface. One side of the first light entering region on the second light entering region side and one side of the second light entering region on the first light entering region side are in contact with each other. The first light exiting region is positioned on a first light receiving region of the first image sensor. The second light exiting region is positioned on a second light receiving region of the second image sensor. One side surface of the first side surface on the second fiber optic plate side and one side surface of the second side surface on the first fiber optic plate side exhibit shapes along each other and in contact with each other.

In this radiation detector, when radiation enters the scintillator layer, light is generated in the scintillator layer. Further, light which has entered the first fiber optic plate from the scintillator layer is guided from the first light entering region to the first light exiting region and enters the first light receiving region of the first image sensor. On the other hand, light which has entered the second fiber optic plate from the scintillator layer is guided from the second light entering region to the second light exiting region and enters the second light receiving region of the second image sensor. Here, the one side of the first light entering region on the second light entering region side and the one side of the second light entering region on the first light entering region side are in contact with each other. For this reason, light generated in the scintillator layer is detected by the first image sensor and the second image sensor in a continuous manner. In addition, the one side surface of the first side surface on the second fiber optic plate side, and the one side surface of the second side surface on the first fiber optic plate side exhibit shapes along each other and in contact with each other. For this reason, a positional deviation is unlikely to occur between the first light entering surface of the first fiber optic plate and the second light entering surface of the second fiber optic plate. Thus, according to this radiation detector, a radiographic image can be accurately obtained over an extended range.

In the radiation detector according to the aspect of the present disclosure, a distance between one side of the first light exiting region on the second light exiting region side and one side of the second light exiting region on the first light exiting region side may be longer than a distance between one side of the first light receiving region on the second light receiving region side and one side of the second light receiving region on the first light receiving region side. The one side of the first light exiting region on the second light exiting region side may be positioned on the one side of the first light receiving region on the second light receiving region side or on a side inward from the one side of the first light receiving region on the second light receiving region side. The one side of the second light exiting region on the first light exiting region side may be positioned on the one side of the second light receiving region on the first light receiving region side or on a side inward from the one side of the second light receiving region on the first light receiving region side. According to this constitution, while positioning accuracy of the first fiber optic plate and the second fiber optic plate with respect to the first image sensor and the second image sensor is relaxed, light guided by each of the first fiber optic plate and the second fiber optic plate can be reliably detected by the first image sensor and the second image sensor.

The radiation detector according to the aspect of the present disclosure may further include a storage portion provided on the wiring board. The storage portion may store a first deviation amount between the one side of the first light exiting region on the second light exiting region side and the one side of the first light receiving region on the second light receiving region side and a second deviation amount between the one side of the second light exiting region on the first light exiting region side and the one side of the second light receiving region on the first light receiving region side. According to this constitution, one continuous radiographic image can be generated on the basis of the first deviation amount and the second deviation amount.

In the radiation detector according to the aspect of the present disclosure, an outer edge of the first light entering surface and the second light entering surface continuous with each other and an outer edge of the first light exiting surface and the second light exiting surface continuous with each other may include the first light receiving region and the second light receiving region when viewed in a thickness direction of the wiring board. According to this constitution, on radiation entering sides of the first light receiving region and the second light receiving region, the first fiber optic plate and the second fiber optic plate are present with a sufficient thickness (that is, a thickness corresponding to a distance between the first light entering surface and the first light exiting surface and a thickness corresponding to a distance between the second light entering surface and the second light exiting surface). Therefore, deterioration due to radiation of the first light receiving region and the second light receiving region can be curbed.

In the radiation detector according to the aspect of the present disclosure, the first image sensor may have a first circuit region adjacent to the first light receiving region. The second image sensor may have a second circuit region adjacent to the second light receiving region. The outer edge of the first light entering surface and the second light entering surface continuous with each other and the outer edge of the first light exiting surface and the second light exiting surface continuous with each other may include the first light receiving region, the first circuit region, the second light receiving region, and the second circuit region when viewed in the thickness direction of the wiring board. According to this constitution, on the radiation entering sides of the first light receiving region, the first circuit region, the second light receiving region, and the second circuit region, the first fiber optic plate and the second fiber optic plate are present with a sufficient thickness (that is, a thickness corresponding to the distance between the first light entering surface and the first light exiting surface and a thickness corresponding to the distance between the second light entering surface and the second light exiting surface). Therefore, deterioration due to radiation of the first light receiving region, the first circuit region, the second light receiving region, and the second circuit region can be curbed.

According to another aspect of the present disclosure, there is provided a method for manufacturing the radiation detector described above. The method includes a step of acquiring the first fiber optic plate and the second fiber optic plate bonded to each other on the one side surface of the first side surface on the second fiber optic plate side and the one side surface of the second side surface on the first fiber optic plate side, a step of polishing the first light entering surface of the first fiber optic plate and the second light entering surface of the second fiber optic plate after the step of acquiring, and a step of forming the scintillator layer on the first fiber optic plate and the second fiber optic plate and bonding the first fiber optic plate and the second fiber optic plate onto the first image sensor and the second image sensor mounted on the wiring board after the step of polishing.

In this method for manufacturing the radiation detector, through the step of acquiring the first fiber optic plate and the second fiber optic plate bonded to each other and the step of polishing the first light entering surface of the first fiber optic plate and the second light entering surface of the second fiber optic plate, the first light entering surface of the first fiber optic plate and the second light entering surface of the second fiber optic plate can be made flush with each other easily and reliably. Moreover, in a state in which the first light entering surface and the second light entering surface are flush with each other, occurrence of a distortion or the like in the scintillator layer can be curbed through the step of forming the scintillator layer. Thus, according to this radiation detector manufacturing method, a radiation detector capable of accurately acquiring a radiographic image over an extended range can be reliably manufactured.

In the method for manufacturing the radiation detector according to the aspect of the present disclosure, in the step of bonding, the scintillator layer may be formed on the first fiber optic plate and the second fiber optic plate, and thereafter the first fiber optic plate and the second fiber optic plate may be bonded onto the first image sensor and the second image sensor mounted on the wiring board. In this case, inspection of the scintillator layer formed on the first fiber optic plate and the second fiber optic plate can be performed before they are bonded to the first image sensor and the second image sensor which are relatively expensive. Therefore, for example, when there is a defect in the scintillator layer, the first image sensor and the second image sensor are not wasted. As a result, increase in manufacturing costs can be curbed.

In the method for manufacturing the radiation detector according to the aspect of the present disclosure, the scintillator layer may be formed of CsI. Here, the scintillator layer is formed in advance on the first fiber optic plate and the second fiber optic plate. Therefore, occurrence of damage to the first image sensor, the second image sensor, and the wiring board caused by corrosiveness of CsI can be curbed.

In the method for manufacturing the radiation detector according to the aspect of the present disclosure, in the step of bonding, the first fiber optic plate and the second fiber optic plate may be bonded onto the first image sensor and the second image sensor mounted on the wiring board, and thereafter the scintillator layer may be formed on the first fiber optic plate and the second fiber optic plate. In this case, the scintillator layer having a lower strength than other members is formed last. Therefore, occurrence of damage to the scintillator layer can be curbed.

In the method for manufacturing the radiation detector according to the aspect of the present disclosure, in the step of polishing, the first light entering surface of the first fiber optic plate and the second light entering surface of the second fiber optic plate may be polished, and the first light exiting surface of the first fiber optic plate and the second light exiting surface of the second fiber optic plate may be polished. In this case, in the step of bonding the first fiber optic plate and the second fiber optic plate onto the first image sensor and the second image sensor, the distance between the first light exiting region of the first fiber optic plate and the first light receiving region of the first image sensor and the distance between the second light exiting region of the second fiber optic plate and the second light receiving region of the second image sensor can be made uniform. Thus, in this case, a radiation detector capable of accurately acquiring a radiographic image over an extended range can be more reliably manufactured.

According to another aspect of the present disclosure, there is provided a method for manufacturing the radiation detector described above. The method includes a step of forming the scintillator layer on the first fiber optic plate and the second fiber optic plate and bonding the first fiber optic plate and the second fiber optic plate onto the first image sensor and the second image sensor mounted on the wiring board, a step of measuring the first deviation amount and the second deviation amount after the step of forming and bonding, and a step of storing the first deviation amount and the second deviation amount in the storage portion provided on the wiring board after the step of measuring.

According to this radiation detector manufacturing method, unique first and second deviation amounts are stored in the storage portion in an individual radiation detector. Therefore, a radiation detector capable of accurately generating one radiographic image on the basis of the stored first and second deviation amounts can be manufactured.

According to another aspect of the present disclosure, there is provided an image processing method using the radiation detector described above. The image processing method includes a step of acquiring a first deviation amount between the one side of the first light exiting region on the second light exiting region side and the one side of the first light receiving region on the second light receiving region side and a second deviation amount between the one side of the second light exiting region on the first light exiting region side and the one side of the second light receiving region on the first light receiving region side, and a step of generating one radiographic image on the basis of a first electrical signal output from the first image sensor via the wiring board, a second electrical signal output from the second image sensor via the wiring board, the first deviation amount, and the second deviation amount after the step of acquiring.

According to this processing method, unique first and second deviation amounts are acquired in an individual radiation detector. Therefore, one radiographic image can be accurately generated on the basis of the acquired first and second deviation amounts.

Advantageous Effects of Invention

According to the present disclosure, a radiographic image can be accurately obtained over an extended range.

BRIEF DESCRIPTION OF DRAWINGS

FIG. 4 is a view for illustrating a method for manufacturing the radiation detector according to the embodiment.

FIG. 5 is another view for illustrating the method for manufacturing the radiation detector according to the embodiment.

FIG. 12 is another view for illustrating the modification example of the radiation detector.

DESCRIPTION OF EMBODIMENT

Hereinafter, an embodiment of the present disclosure will be described in detail with reference to the drawings. In each of the drawings, the same reference signs are applied to parts which are the same or corresponding, and duplicate description will be omitted.

[Constitution of Radiation Detector]

Figure 1:
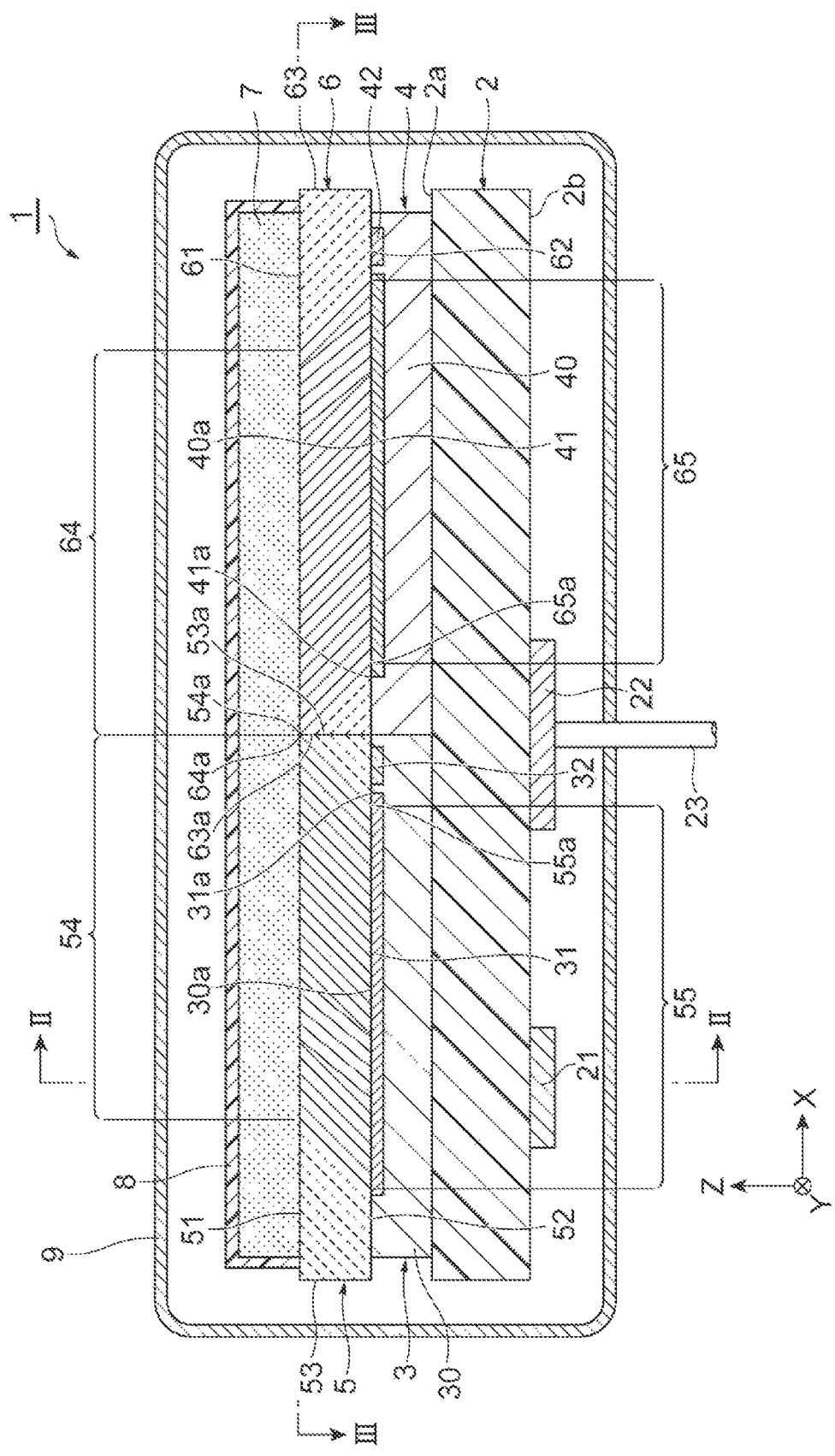
FIG. 1 is a cross-sectional view of a radiation detector according to an embodiment.
Figure 2:
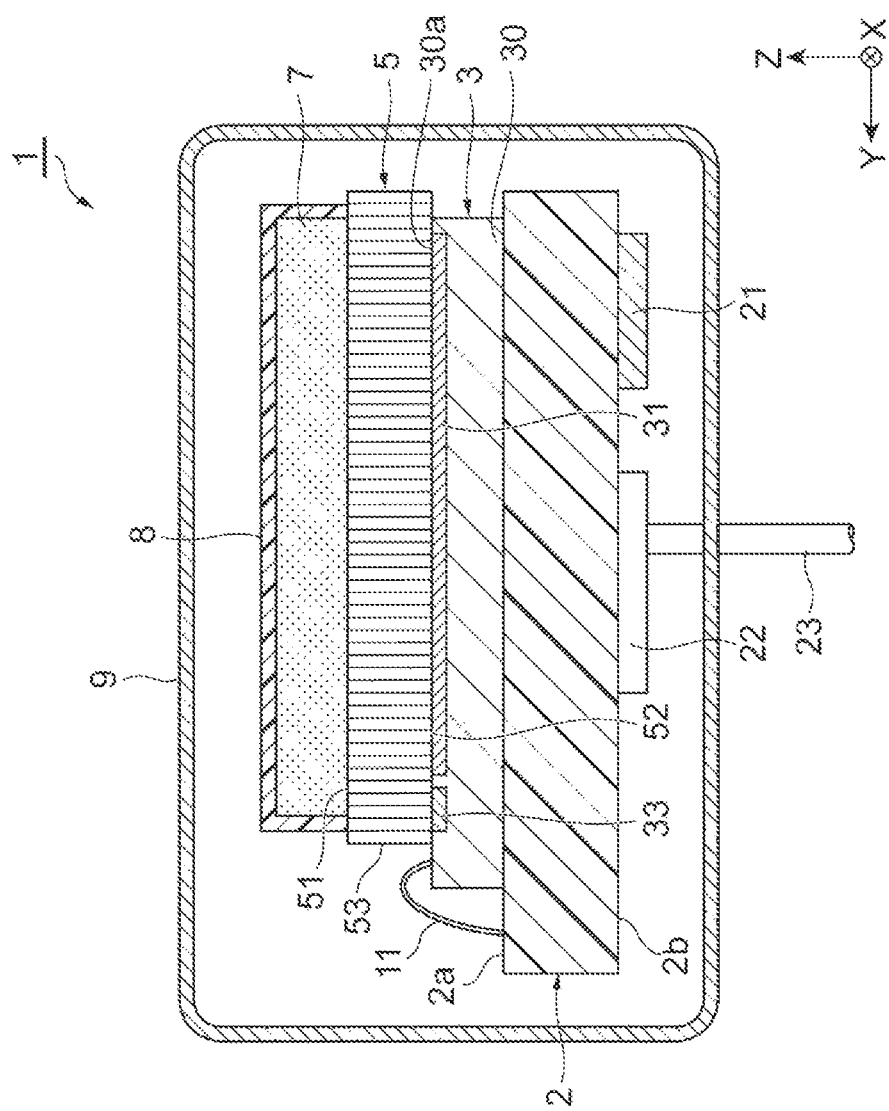
FIG. 2 is a cross-sectional view of the radiation detector shown in FIG. 1 along line II-II.

As shown in FIGS. 1 and 2, a radiation detector 1 includes a wiring board 2, a first image sensor 3, a second image sensor 4, a first fiber optic plate (first FOP) 5, a second fiber optic plate (FOP) 6, a scintillator layer 7, a protective layer 8, and a casing 9. The wiring board 2 has a front surface 2a and a rear surface 2b facing each other. Hereinafter, each constituent will be described in detail having one direction parallel to the front surface 2a and the rear surface 2b as an X axis direction, a direction parallel to the front surface 2a and the rear surface 2b and parallel to the X axis direction as a Y axis direction, and a direction in which the front surface 2a and the rear surface 2b face each other (thickness direction of the wiring board 2) as a Z axis direction.

The first image sensor 3 and the second image sensor 4 are adjacent to each other on the wiring board 2. More specifically, the first image sensor 3 and the second image sensor 4 are mounted on the front surface 2a of the wiring board 2 and are adjacent to each other in the X axis direction.

The first image sensor 3 is constituted by providing a first light receiving region 31 and first circuit regions 32 and 33 on a first semiconductor substrate 30. For example, the first image sensor 3 is a solid-state image capturing element such as a CCD or a CMOS. The first light receiving region 31 is constituted of a plurality of pixels performing photoelectric conversion. The first circuit regions 32 and 33 are signal reading circuits such as shift registers.

The first light receiving region 31 is provided on a front surface 30a on a side opposite to the wiring board 2 in the first semiconductor substrate 30. The first light receiving region 31 exhibits a rectangular shape having a pair of sides perpendicular to the X axis direction and a pair of sides perpendicular to the Y axis direction, for example, when viewed in the Z axis direction. Each of the first circuit regions 32 and 33 is adjacent to the first light receiving region 31. More specifically, the first circuit region 32 is provided on the second image sensor 4 side with respect to the first light receiving region 31. The first circuit region 33 is provided on one side in the Y axis direction with respect to the first light receiving region 31. Each of the first circuit regions 32 and 33 is electrically connected to the wiring board 2 using a wire 11.

The second image sensor 4 is constituted by providing a second light receiving region 41 and second circuit regions 42 and 43 (refer to FIG. 3) on a second semiconductor substrate 40. For example, the second image sensor 4 is a solid-state image capturing element such as a CCD or a CMOS. The second light receiving region 41 is constituted of a plurality of pixels performing photoelectric conversion. The second circuit regions 42 and 43 are signal reading circuits such as shift registers.

The second light receiving region 41 is provided on a front surface 40a on a side opposite to the wiring board 2 in the second semiconductor substrate 40. The second light receiving region 41 exhibits a rectangular shape having a pair of sides perpendicular to the X axis direction and a pair of sides perpendicular to the Y axis direction, for example, when viewed in the Z axis direction. Each of the second circuit regions 42 and 43 is adjacent to the second light receiving region 41. More specifically, the second circuit region 42 is provided on a side opposite to the first image sensor 3 with respect to the second light receiving region 41. The second circuit region 43 is provided on one side in the Y axis direction with respect to the second light receiving region 41. Each of the second circuit regions 42 and 43 is electrically connected to the wiring board 2 using the wire 11.

The first FOP 5 and the second FOP 6 are adjacent to each other on the first image sensor 3 and the second image sensor 4. More specifically, the first FOP 5 and the second FOP 6 are fixed to the front surface 30a of the first semiconductor substrate 30 and the front surface 40a of the second semiconductor substrate 40 using an adhesive or the like and are adjacent to each other in the X axis direction.

The first FOP 5 has a first light entering surface 51, a first light exiting surface 52, and a first side surface 53. The first light entering surface 51 is a surface on a side opposite to the first image sensor 3. The first light exiting surface 52 is a surface on the first image sensor 3 side. The first side surface 53 is a surface connecting the first light entering surface 51 and the first light exiting surface 52. For example, the first FOP 5 exhibits a rectangular shape having a pair of side surfaces perpendicular to the X axis direction and a pair of side surfaces perpendicular to the Y axis direction as the first side surface 53.

Each of a plurality of optical fibers constituting the first FOP 5 is inclined in a state of forming an angle of 67°, for example, with respect to each of the first light entering surface 51 and the first light exiting surface 52 such that a light exiting end is positioned on a side opposite to the second FOP 6 in the X axis direction with respect to a light entering end. In the first FOP 5, optical fibers having the light entering ends positioned on the first light entering surface 51 and the light exiting ends positioned on the first light exiting surface 52 are optical fibers capable of guiding light from the first light entering surface 51 to the first light exiting surface 52. In the first FOP 5, a first light entering region 54 is formed on the first light entering surface 51 due to the light entering ends of the plurality of optical fibers capable of guiding light, and a first light exiting region 55 is formed on the first light exiting surface 52 due to the light exiting ends of the plurality of optical fibers capable of guiding light. That is, in the first FOP 5, light can be guided between the first light entering region 54 of the first light entering surface 51 and the first light exiting region 55 of the first light exiting surface 52. For example, each of the first light entering region 54 and the first light exiting region 55 exhibits a rectangular shape having a pair of sides perpendicular to the X axis direction and a pair of sides perpendicular to the Y axis direction.

The second FOP 6 has a second light entering surface 61, a second light exiting surface 62, and a second side surface 63. The second light entering surface 61 is a surface on a side opposite to the second image sensor 4. The second light exiting surface 62 is a surface on the second image sensor 4 side. The second side surface 63 is a surface connecting the second light entering surface 61 and the second light exiting surface 62. For example, the second FOP 6 exhibits a rectangular shape having a pair of side surfaces perpendicular to the X axis direction and a pair of side surfaces perpendicular to the Y axis direction as the second side surface 63.

Each of a plurality of optical fibers constituting the second FOP 6 is inclined in a state of forming an angle of 67°, for example, with respect to each of the second light entering surface 61 and the second light exiting surface 62 such that a light exiting end is positioned on a side opposite to the first FOP 5 in the X axis direction with respect to a light entering end. In the second FOP 6, optical fibers having the light entering ends positioned on the second light entering surface 61 and the light exiting ends positioned on the second light exiting surface 62 are optical fibers capable of guiding light from the second light entering surface 61 to the second light exiting surface 62. In the second FOP 6, a second light entering region 64 is formed on the second light entering surface 61 due to the light entering ends of the plurality of optical fibers capable of guiding light, and a second light exiting region 65 is formed on the second light exiting surface 62 due to the light exiting ends of the plurality of optical fibers capable of guiding light. That is, in the second FOP 6, light can be guided between the second light entering region 64 of the second light entering surface 61 and the second light exiting region 65 of the second light exiting surface 62. For example, each of the second light entering region 64 and the second light exiting region 65 exhibits a rectangular shape having a pair of sides perpendicular to the X axis direction and a pair of sides perpendicular to the Y axis direction.

One side 54a of the first light entering region 54 on the second light entering region 64 side and one side 64a of the second light entering region 64 on the first light entering region 54 side are in contact (line contact) with each other. The first light exiting region 55 is positioned on the first light receiving region 31 of the first image sensor 3. One side 55a of the first light exiting region 55 on the second light exiting region 65 side is positioned on one side 31a of the first light receiving region 31 on the second light receiving region 41 side or on a side inward from the one side 31a. The second light exiting region 65 is positioned on the second light receiving region 41 of the second image sensor 4. One side 65a of the second light exiting region 65 on the first light exiting region 55 side is positioned on one side 41a of the second light receiving region 41 on the first light receiving region 31 side or on a side inward from the one side 41a. A distance between the one side 55a of the first light exiting region 55 and the one side 65a of the second light exiting region 65 is longer than a distance between the one side 31a of the first light receiving region 31 and the one side 41a of the second light receiving region 41. Here, when viewed in the Z axis direction, an outer edge of the first light receiving region 31 includes an outer edge of the first light exiting region 55, and an outer edge of the second light receiving region 41 includes an outer edge of the second light exiting region 65.

Here, when each of the plurality of optical fibers constituting the first FOP 5 is inclined such that the light exiting end is positioned on a side opposite to the second FOP 6 in the X axis direction with respect to the light entering end, an angle (inclination angle) formed by each of the plurality of optical fibers constituting the first FOP 5 and each of the first light entering surface 51 and the first light exiting surface 52 is regarded as θ1. In addition, when each of the plurality of optical fibers constituting the second FOP 6 is inclined such that the light exiting end is positioned on a side opposite to the first FOP 5 in the X axis direction with respect to the light entering end, an angle (inclination angle) formed by each of the plurality of optical fibers constituting the second FOP 6 and each of the second light entering surface 61 and the second light exiting surface 62 is regarded as θ2. Moreover, a thickness of each of the first FOP 5 and the second FOP 6 is regarded as T. In this case, when the distance between the one side 55a of the first light exiting region 55 and the one side 65a of the second light exiting region 65 is regarded as D1, it is expressed as D1=T(1/tan θ1+1/tan θ2). Therefore, when the distance between the one side 31a of the first light receiving region 31 and the one side 41a of the second light receiving region 41 is regarded as D2, the inclination angle θ1 of the plurality of optical fibers constituting the first FOP 5 and the inclination angle θ2 of the plurality of optical fibers constituting the second FOP 6 may be determined such that D1>D2, that is, T(1/tan θ1+1/tan θ2)>D2 is satisfied.

Figure 3:
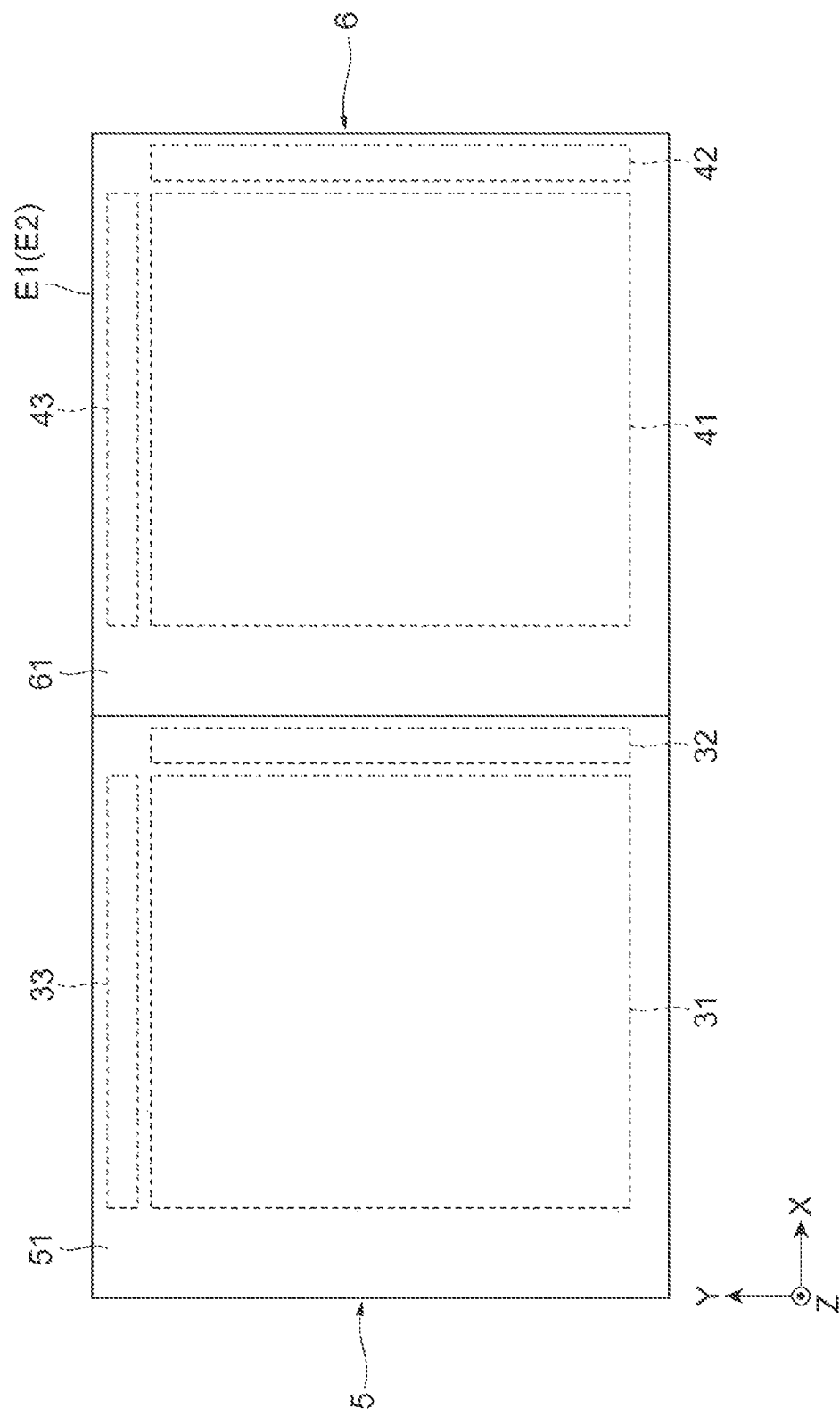
FIG. 3 is a cross-sectional view of the radiation detector shown in FIG. 1 along line III-III.

As shown in FIG. 3, when viewed in the Z axis direction, an outer edge E1 of the first light entering surface 51 and the second light entering surface 61 continuous with each other include the first light receiving region 31, the first circuit regions 32 and 33, the second light receiving region 41, and the second circuit regions 42 and 43. Similarly, when viewed in the Z axis direction, an outer edge E2 of the first light exiting surface 52 and the second light exiting surface 62 continuous with each other include the first light receiving region 31, the first circuit regions 32 and 33, the second light receiving region 41, and the second circuit regions 42 and 43. In FIG. 3, illustration of the casing 9 is omitted.

As shown in FIGS. 1 and 2, one side surface 53a of the first side surface 53 of the first FOP 5 on the second FOP 6 side and one side surface 63a of the second side surface 63 of the second FOP 6 on the first FOP 5 side exhibit shapes along each other and in contact (surface contact) with each other. The first FOP 5 and the second FOP 6 are bonded to each other using an adhesive or the like on the one side surface 53a and the one side surface 63a in contact with each other. In a state in which the first FOP 5 and the second FOP 6 are bonded to each other, the first light entering surface 51 and the second light entering surface 61 are positioned in the same plane (for example, a plane perpendicular to a Z axis), and the first light exiting surface 52 and the second light exiting surface 62 are positioned in the same plane (for example, a plane perpendicular to the Z axis).

The scintillator layer 7 is provided on the first FOP 5 and the second FOP 6. More specifically, the scintillator layer 7 is formed on the first light entering surface 51 of the first FOP 5 and the second light entering surface 61 of the second FOP 6 such that the first light entering region 54 and the second light entering region 64 are covered. For example, the scintillator layer 7 is formed of CsI, GOS, or the like and generates light in response to entry of radiation.

The protective layer 8 covers a front surface of the front surface of the scintillator layer 7 except for the front surface which comes into contact with the first FOP 5 and the second FOP 6. For example, the protective layer 8 is formed of parylene or the like and protects the scintillator layer 7 from moisture or the like.

The casing 9 accommodates the wiring board 2, the first image sensor 3, the second image sensor 4, the first FOP 5, the second FOP 6, the scintillator layer 7, and the protective layer 8. For example, the casing 9 is formed of plastic, which protects the wiring board 2, the first image sensor 3, the second image sensor 4, the first FOP 5, the second FOP 6, the scintillator layer 7, and the protective layer 8 from an external force or the like and allows radiation to be transmitted therethrough.

On the wiring board 2, a storage portion 21 and an electrode pad 22 are provided. For example, the storage portion 21 is constituted of a memory. A cable 23 extending to the outside via a wall part of the casing 9 is connected to the electrode pad 22. The cable 23 is used for inputting and outputting an electrical signal with respect to the wiring board 2, supplying power, and the like.

The storage portion 21 stores a first deviation amount between the one side 55a of the first light exiting region 55 of the first FOP 5 and the one side 31a of the first light receiving region 31 of the first image sensor 3 and a second deviation amount between the one side 65a of the second light exiting region 65 of the second FOP 6 and the one side 41a of the second light receiving region 41 of the second image sensor 4. When the one side 55a of the first light exiting region 55 is positioned on the one side 31a of the first light receiving region 31, the storage portion 21 stores zero for the first deviation amount. When the one side 65a of the second light exiting region 65 is positioned on the one side 41a of the second light receiving region 41, the storage portion 21 stores zero for the second deviation amount.

[Radiation Detector Manufacturing Method]

A method for manufacturing the radiation detector 1 described above will be described. First, as shown in (a) of FIG. 4, a FOP block 10 is prepared. As schematically indicated by a two-dot dashed line in (a) of FIG. 4, a plurality of optical fibers constituting the FOP block 10 extends in a direction perpendicular to a main surface 10a of the FOP block 10. Subsequently, the FOP block 10 is cut along a surface inclining in a state of forming an angle of 23°, for example, with respect to the main surface 10a, thereby obtaining a first FOP block 50 and a second FOP block 60 having a rectangular parallelepiped shape as shown in (b) of FIG. 4. As schematically indicated by a two-dot dashed line in (b) of FIG. 4, each of a plurality of optical fibers constituting the first FOP block 50 is inclined in a state of forming an angle of 67°, for example, with respect to a first main surface 50a of the first FOP block 50. Similarly, each of a plurality of optical fibers constituting the second FOP block 60 is inclined in a state of forming an angle of 67°, for example, with respect to a second main surface 60a of the second FOP block 60.

Subsequently, as shown in (a) of FIG. 5, the first FOP block 50 and the second FOP block 60 are bonded to each other using an adhesive or the like such that the plurality of optical fibers constituting the first FOP block 50 and the plurality of optical fibers constituting the second FOP block 60 are separated from each other to an extent that they are separated from the first main surface 50a and the second main surface 60a. Subsequently, as shown in (b) of FIG. 5, the first FOP block 50 and the second FOP block 60 bonded to each other are cut along a surface perpendicular to the first main surface 50a and the second main surface 60a and a surface parallel to the same, thereby obtaining a plurality of first FOPs 5 and a plurality of second FOPs 6 bonded to each other as shown in (c) of FIG. 5. The foregoing process is a step of acquiring the first FOP 5 and the second FOP 6 bonded to each other on the one side surface 53a of the first side surface 53 and the one side surface 63a of the second side surface 63.

Subsequently, the first light entering surface 51 of the first FOP 5 and the second light entering surface 61 of the second FOP 6 are polished, and the first light exiting surface 52 of the first FOP 5 and the second light exiting surface 62 of the second FOP 6 are polished (step of polishing). Accordingly, the first light entering surface 51 and the second light entering surface 61 are flush with each other, and the first light exiting surface 52 and the second light exiting surface 62 are flush with each other. The first light entering surface 51 and the second light entering surface 61 may be polished, and thereafter the first light exiting surface 52 and the second light exiting surface 62 may be polished. Alternatively, the first light exiting surface 52 and the second light exiting surface 62 may be polished, and thereafter the first light entering surface 51 and the second light entering surface 61 may be polished.

Figure 6:
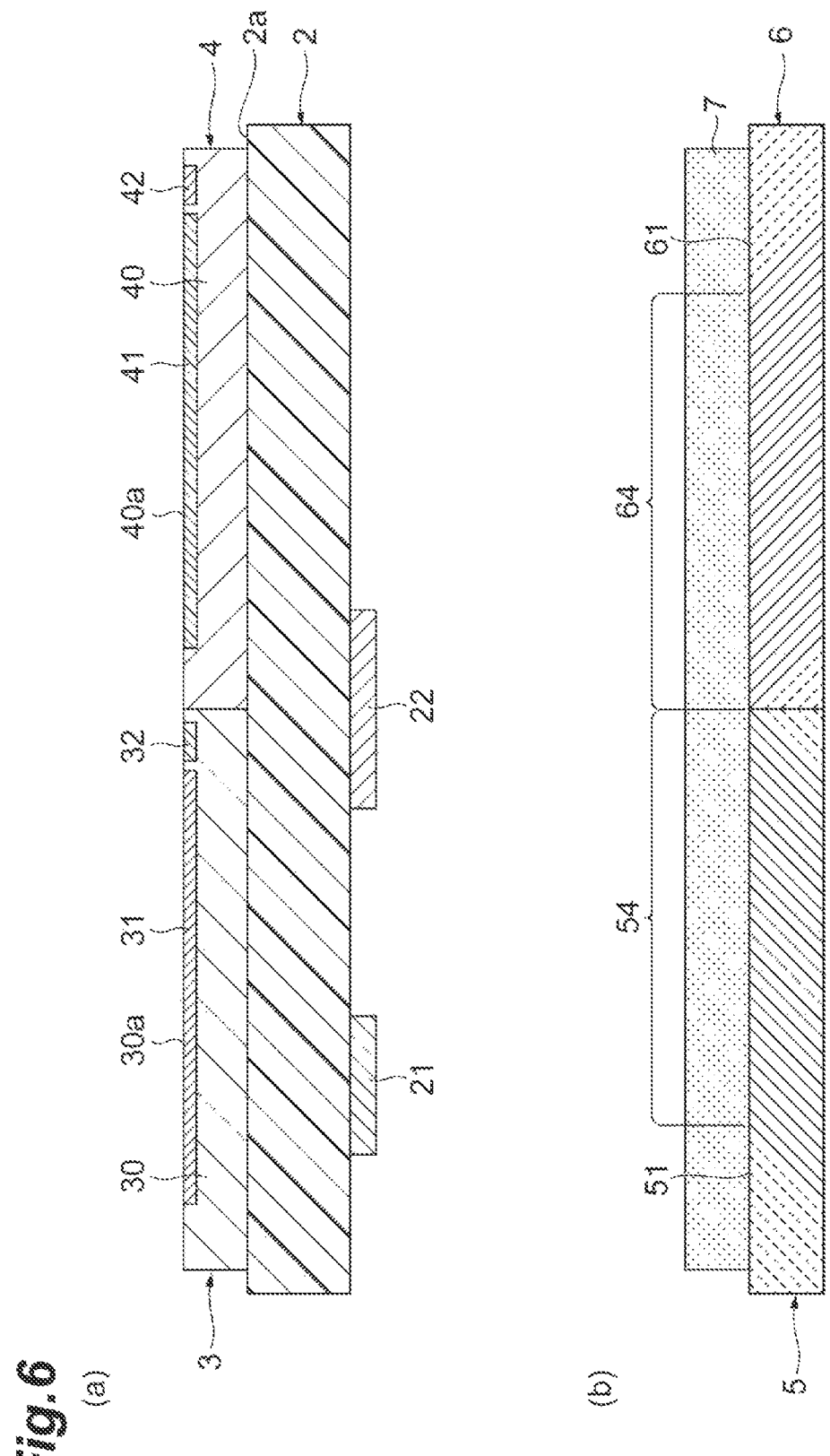
FIG. 6 is another view for illustrating the method for manufacturing the radiation detector according to the embodiment.

On the other hand, as shown in (a) of FIG. 6, the first image sensor 3 and the second image sensor 4 are mounted on the wiring board 2 provided with the storage portion 21 and the electrode pad 22. In addition, as shown in (b) of FIG. 6, the scintillator layer 7 is formed on the first FOP 5 and the second FOP 6 such that the first light entering region 54 of the first FOP 5 and the second light entering region 64 of the second FOP 6 are covered (step of forming and bonding). Here, the scintillator layer 7 is formed on the first FOP 5 and the second FOP 6 by performing vapor deposition of a scintillator material on the first FOP 5 and the second FOP 6. Subsequently, as shown in (a) of FIG. 7, the protective layer 8 is formed so as to cover a front surface of the front surface of the scintillator layer 7 except for the front surface which comes into contact with the first FOP 5 and the second FOP 6.

Figure 7:
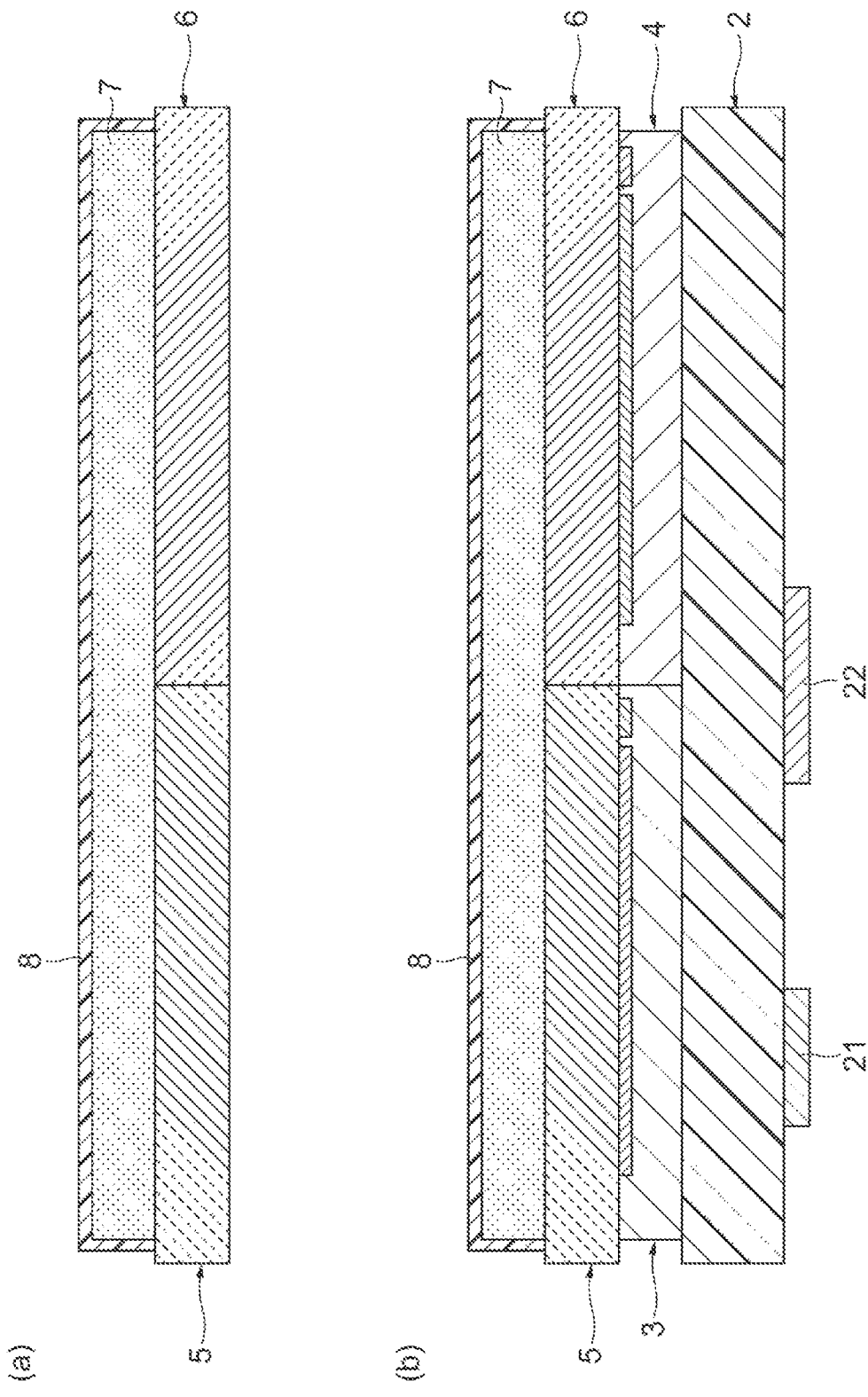
FIG. 7 is another view for illustrating the method for manufacturing the radiation detector according to the embodiment.

Subsequently, as shown in (b) of FIG. 7, the first FOP 5 and the second FOP 6 provided with the scintillator layer 7 and the protective layer 8 are bonded onto the first image sensor 3 and the second image sensor 4 mounted on the wiring board 2 using an adhesive or the like (step of forming and bonding). At this time, positioning is performed such that the first light exiting region 55 of the first FOP 5 is positioned on the first light receiving region 31 of the first image sensor 3 and the second light exiting region 65 of the second FOP 6 is positioned on the second light receiving region 41 of the second image sensor 4. The first FOP 5 and the second FOP 6 may be bonded onto the first image sensor 3 and the second image sensor 4 mounted on the wiring board 2, and thereafter the scintillator layer 7 may be formed on the first FOP 5 and the second FOP 6. For example, when the scintillator layer 7 is a film type, the scintillator layer 7 can be formed on the first FOP 5 and the second FOP 6 by bonding the first FOP 5 and the second FOP 6 onto the first image sensor 3 and the second image sensor 4 and thereafter pasting the scintillator layer 7 on the first FOP 5 and the second FOP 6.

Subsequently, as shown in FIG. 1, the wiring board 2, the first image sensor 3, the second image sensor 4, the first FOP 5, the second FOP 6, the scintillator layer 7, and the protective layer 8 are accommodated in the casing 9, and the cable 23 connected to the electrode pad 22 of the wiring board 2 is drawn out to the outside via the wall part of the casing 9.

Subsequently, the cable 23 is connected to an image processing device, and a radiographic image is acquired regarding a reference prepared in advance. Here, when the one side 55a of the first light exiting region 55 of the first FOP 5 is positioned on a side inward from the one side 31a of the first light receiving region 31 of the first image sensor 3, a region lacking in pixel value is generated in a radiographic image regarding the reference as much as the first deviation amount between the one side 55a of the first light exiting region 55 and the one side 31a of the first light receiving region 31. Similarly, when the one side 65a of the second light exiting region 65 of the second FOP 6 is positioned on a side inward from the one side 41a of the second light receiving region 41 of the second image sensor 4, a region lacking in pixel value is generated in a radiographic image regarding the reference as much as the second deviation amount between the one side 65a of the second light exiting region 65 and the one side 41a of the second light receiving region 41. Here, the first deviation amount and the second deviation amount are measured on the basis of the radiographic image regarding the reference (step of measuring).

Subsequently, the first deviation amount and the second deviation amount are stored in the storage portion 21 provided on the wiring board 2 (step of storing). When the one side 55a of the first light exiting region 55 is positioned on the one side 31a of the first light receiving region 31, the first deviation amount is zero. Similarly, when the one side 65a of the second light exiting region 65 is positioned on the one side 41a of the second light receiving region 41, the second deviation amount is zero. In this way, the radiation detector 1 is obtained.

[Image Processing Method]

An image processing method using the radiation detector 1 described above will be described. Here, a case in which an intraoral X-ray transmission image is acquired as a radiographic image will be described.

First, the cable 23 is connected to the image processing device. A signal transmission part may be provided on the wiring board 2, and the wiring board 2 and the image processing device may be connected to each other by radio. Subsequently, the image processing device acquires the first deviation amount and the second deviation amount from the storage portion 21 via the cable 23 (step of acquiring). Subsequently, the casing 9 is disposed inside the mouth, and image capturing of an intraoral X-ray transmission image is performed. Subsequently, the image processing device acquires a first electrical signal output from the first image sensor 3 and a second electrical signal output from the second image sensor 4 via the wiring board 2 and the cable 23. Subsequently, the image processing device generates one X-ray transmission image on the basis of the first electrical signal, the second electrical signal, the first deviation amount, and the second deviation amount (step of generating).

Figure 8:
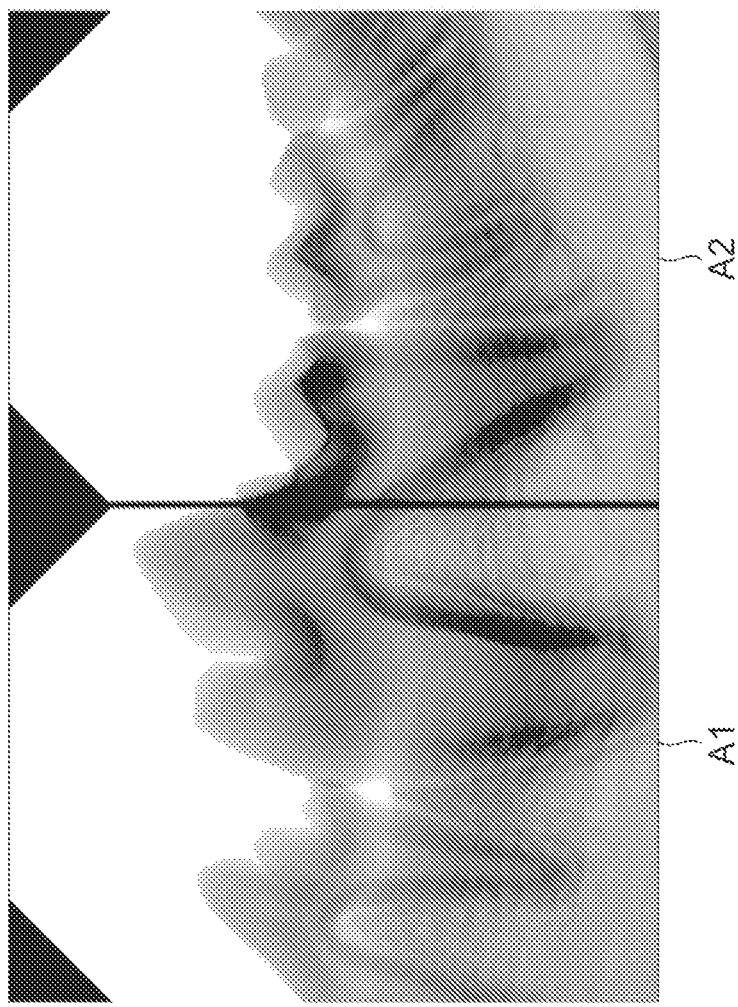
FIG. 8 is a view for illustrating an image processing method according to the embodiment.
Figure 9:
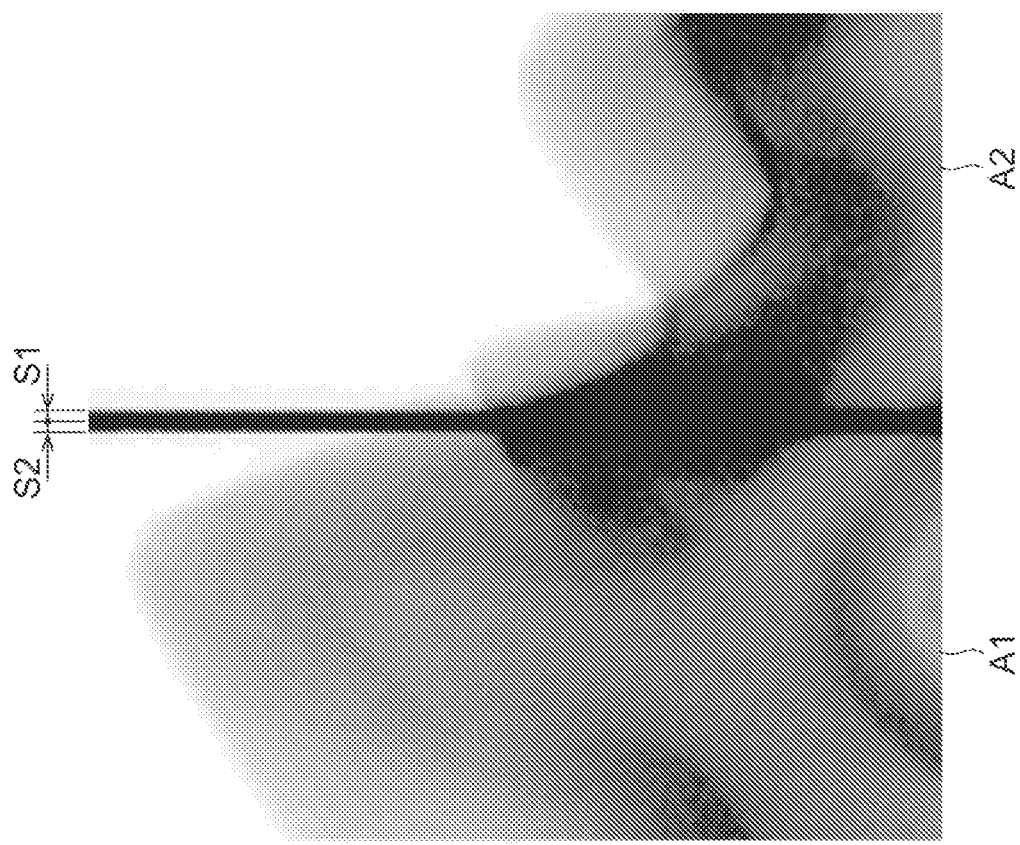
FIG. 9 is another view for illustrating the image processing method according to the embodiment.
Figure 10:
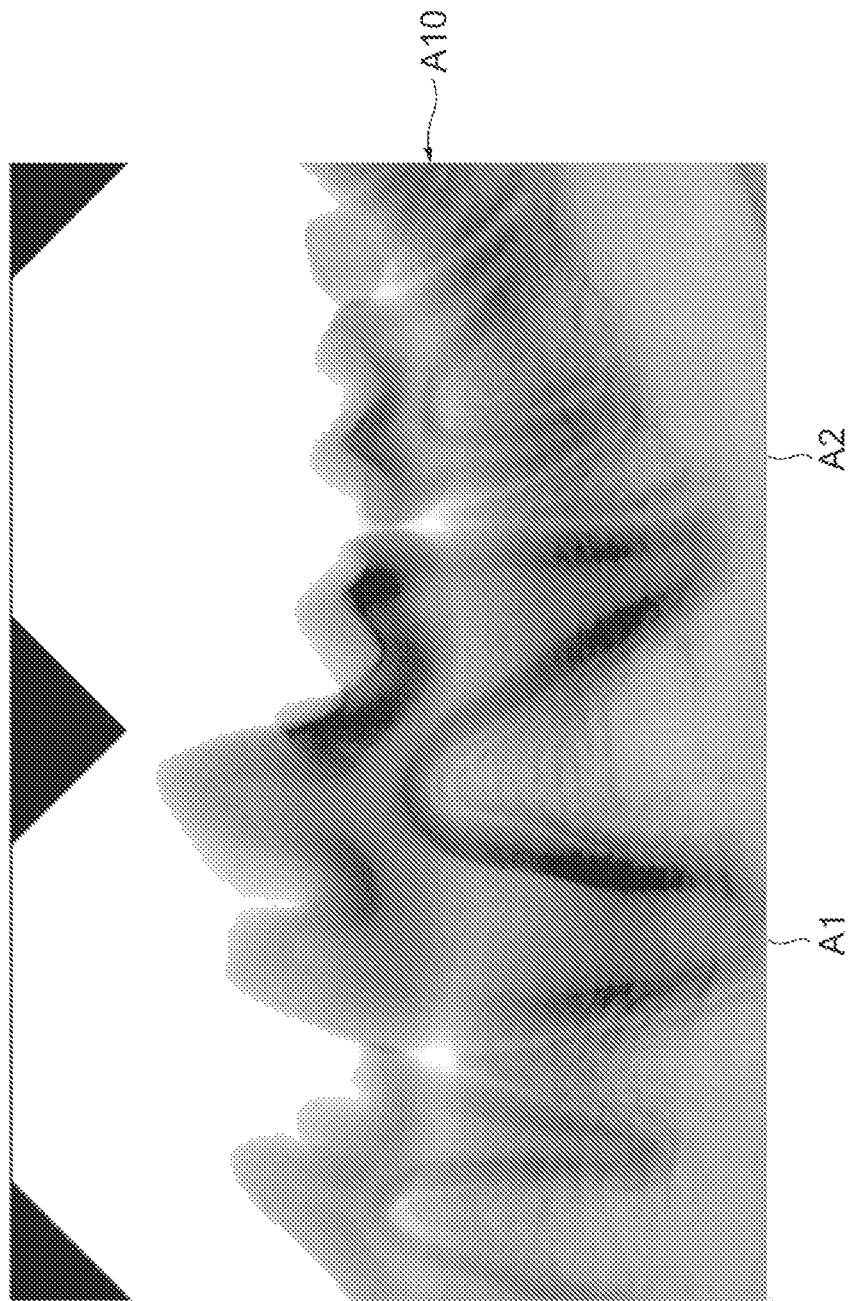
FIG. 10 is another view for illustrating the image processing method according to the embodiment.

More specifically, when the image processing device generates one X-ray transmission image without considering the first deviation amount and the second deviation amount, a gap (a region lacking in pixel value) is formed between an image A1 based on the first electrical signal and an image A2 based on the second electrical signal as shown in FIG. 8. As shown in FIG. 9, the gap corresponds to a first deviation amount S1 and a second deviation amount S2. Here, the image processing device eliminates the gap in consideration of the first deviation amount S1 and the second deviation amount S2, thereby generating one X-ray transmission image A10 in which the image A1 based on the first electrical signal and the image A2 based on the second electrical signal are joined to each other without having a gap therebetween as shown in FIG. 10.

[Operation and Effects]

As described above, in the radiation detector 1, when radiation (for example, X-rays) enters the scintillator layer 7, light is generated in the scintillator layer 7. Further, light which has entered the first FOP 5 from the scintillator layer 7 is guided from the first light entering region 54 to the first light exiting region 55 and enters the first light receiving region 31 of the first image sensor 3. On the other hand, light which has entered the second FOP 6 from the scintillator layer 7 is guided from the second light entering region 64 to the second light exiting region 65 and enters the second light receiving region 41 of the second image sensor 4. Here, the one side 54a of the first light entering region 54 on the second light entering region 64 side and the one side 64a of the second light entering region 64 on the first light entering region 54 side are in contact with each other. For this reason, light generated in the scintillator layer 7 is detected by the first image sensor 3 and the second image sensor 4 in a continuous manner. In addition, the one side surface 53a of the first side surface 53 on the second FOP 6 side and the one side surface 63a of the second side surface 63 on the first FOP 5 side exhibit shapes along each other and in contact with each other. For this reason, a positional deviation is unlikely to occur between the first light entering surface 51 of the first FOP 5 and the second light entering surface 61 of the second FOP 6. Thus, according to the radiation detector 1, a radiographic image can be accurately obtained over an extended range.

In addition, in the radiation detector 1, the distance between the one side 55a of the first light exiting region 55 on the second light exiting region 65 side and the one side 65a of the second light exiting region 65 on the first light exiting region 55 side is longer than the distance between the one side 31a of the first light receiving region 31 on the second light receiving region 41 side and the one side 41a of the second light receiving region 41 on the first light receiving region 31 side. Further, the one side 55a of the first light exiting region 55 on the second light exiting region 65 side is positioned on the one side 31a of the first light receiving region 31 on the second light receiving region 41 side or on a side inward from the one side 31a, and the one side 65a of the second light exiting region 65 on the first light exiting region 55 side is positioned on the one side 41a of the second light receiving region 41 on the first light receiving region 31 side or on a side inward from the one side 41a. According to this constitution, while positioning accuracy of the first FOP 5 and the second FOP 6 with respect to the first image sensor 3 and the second image sensor 4 is relaxed, light guided by each of the first FOP 5 and the second FOP 6 can be reliably detected by the first image sensor 3 and the second image sensor 4.

In addition, in the radiation detector 1, the storage portion 21 provided on the wiring board 2 stores the first deviation amount between the one side 55a of the first light exiting region 55 on the second light exiting region 65 side and the one side 31a of the first light receiving region 31 on the second light receiving region 41 side and the second deviation amount between the one side 65a of the second light exiting region 65 on the first light exiting region 55 side and the one side 41a of the second light receiving region 41 on the first light receiving region 31 side. According to this constitution, one continuous radiographic image can be generated on the basis of the first deviation amount and the second deviation amount.

In addition, in the radiation detector 1, the outer edge E1 of the first light entering surface 51 and the second light entering surface 61 continuous with each other include the first light receiving region 31, the first circuit regions 32 and 33, the second light receiving region 41, and the second circuit regions 42 and 43 (which will hereinafter be referred to as "the first light receiving region 31 and the like") when viewed in the Z axis direction. Similarly, the outer edge E2 of the first light exiting surface 52 and the second light exiting surface 62 continuous with each other include the first light receiving region 31 and the like when viewed in the Z axis direction. According to this constitution, on radiation entering sides of the first light receiving region 31 and the like, the first FOP 5 and the second FOP 6 are present with a sufficient thickness (that is, a thickness corresponds to a distance between the first light entering surface 51 and the first light exiting surface 52 and a thickness corresponds to a distance between the second light entering surface 61 and the second light exiting surface 62). Therefore, deterioration due to radiation of the first light receiving region 31 and the like can be curbed.

In addition, in the radiation detector 1, each of the plurality of optical fibers constituting the first FOP 5 is inclined in a state of forming an angle other than 90° with respect to the first light receiving region 31 of the first image sensor 3, and each of the plurality of optical fibers constituting the second FOP 6 is inclined in a state of forming an angle other than 90° with respect to the second light receiving region 41 of the second image sensor 4. According to this constitution, for example, compared to a case in which each of the plurality of optical fibers constituting the first FOP 5 forms an angle of 90° with respect to the first light receiving region 31, deterioration due to radiation of the first light receiving region 31 can be curbed. Similarly, for example, compared to a case in which each of the plurality of optical fibers constituting the second FOP 6 forms an angle of 90° with respect to the second light receiving region 41, deterioration due to radiation of the second light receiving region 41 can be curbed. Moreover, in both the first FOP 5 and the second FOP 6, each of the plurality of optical fibers constituting the FOPs is inclined. Therefore, a difference is unlikely to occur between a degree of deterioration due to radiation of the first light receiving region 31 and a degree of deterioration due to radiation of the second light receiving region 41, and thus a difference caused by the difference between the degrees of deterioration due to radiation is unlikely to occur between an output value from the first light receiving region 31 and an output value from the second light receiving region 41.

In addition, in the method for manufacturing the radiation detector 1, through the step of acquiring the first FOP 5 and the second FOP 6 bonded to each other and the step of polishing the first light entering surface 51 of the first FOP 5 and the second light entering surface 61 of the second FOP 6, the first light entering surface 51 of the first FOP 5 and the second light entering surface 61 of the second FOP 6 can be made flush with each other easily and reliably. Moreover, in a state in which the first light entering surface 51 and the second light entering surface 61 are flush with each other, occurrence of a distortion or the like in the scintillator layer 7 can be curbed through the step of forming the scintillator layer 7 even when the scintillator layer 7 is formed by vapor deposition or even when the scintillator layer 7 is formed by pasting. Thus, according to the method for manufacturing the radiation detector 1, the radiation detector 1 capable of accurately acquiring a radiographic image over an extended range can be reliably manufactured.

In addition, in the method for manufacturing the radiation detector 1, the scintillator layer 7 is formed on the first FOP 5 and the second FOP 6, and thereafter the first FOP 5 and the second FOP 6 are bonded onto the first image sensor 3 and the second image sensor 4 mounted on the wiring board 2. In this case, inspection of the scintillator layer 7 formed on the first FOP 5 and the second FOP 6 can be performed before they are bonded to the first image sensor 3 and the second image sensor 4 which are relatively expensive. Therefore, for example, when there is a defect in the scintillator layer 7, the first image sensor 3 and the second image sensor 4 are not wasted. As a result, increase in manufacturing costs can be curbed.

In addition, in the method for manufacturing the radiation detector 1, the scintillator layer 7 is formed of CsI. Here, the scintillator layer 7 is formed in advance on the first FOP 5 and the second FOP 6. Therefore, occurrence of damage to the first image sensor 3, the second image sensor 4, and the wiring board 2 caused by corrosiveness of CsI can be curbed.

In addition, in the method for manufacturing the radiation detector 1, in the step of polishing, the first light entering surface 51 of the first FOP 5 and the second light entering surface 61 of the second FOP 6 are polished, and the first light exiting surface 52 of the first FOP 5 and the second light exiting surface 62 of the second FOP 6 are polished. In this case, in the step of bonding the first FOP 5 and the second FOP 6 onto the first image sensor 3 and the second image sensor 4, the distance between the first light exiting region 55 of the first FOP 5 and the first light receiving region 31 of the first image sensor 3 and the distance between the second light exiting region 65 of the second FOP 6 and the second light receiving region 41 of the second image sensor 4 can be made uniform. Thus, in this case, the radiation detector 1 capable of accurately acquiring a radiographic image over an extended range can be more reliably manufactured.

In addition, in the method for manufacturing the radiation detector 1, unique first and second deviation amounts are stored in the storage portion 21 in the individual radiation detector 1. Therefore, the radiation detector 1 capable of accurately generating one radiographic image on the basis of the stored first and second deviation amounts can be manufactured.

In addition, in the image processing method using the radiation detector 1, unique first and second deviation amounts are acquired in the individual radiation detector 1. Therefore, one radiographic image can be accurately generated on the basis of the acquired first and second deviation amounts.

[Modification Example]

The present disclosure is not limited to the embodiment described above. For example, each of the first light entering region 54 of the first FOP 5 and the second light entering region 64 of the second FOP 6 may exhibit a shape other than a rectangular shape (for example, a polygonal shape other than a rectangular shape) as long as the one side 54*a* of the first light entering region 54 and the one side 64*a* of the second light entering region 64 are in contact (line contact) with each other. Optical fibers not capable of guiding light (for example, optical fibers lacking a part of the light entering ends) may also be partially present along the one side 54*a* of the first light entering region 54. Similarly, optical fibers not capable of guiding light (for example, optical fibers lacking a part of the light entering ends) may also be partially present along the one side 64*a* of the second light entering region 64.

In addition, each of the first FOP 5 and the second FOP 6 may exhibit a shape other than a rectangular plate shape (for example, a polygonal plate shape other than a rectangular plate shape) as long as the one side surface 53*a* of the first side surface 53 and the one side surface 63*a* of the second side surface 63 exhibit shapes along each other and in contact (surface contact) with each other. As an example, the one side surface 53*a* and the one side surface 63*a* may be inclined at an angle other than 90° with respect to the first light entering surface 51 and the second light entering surface 61.

Figure 11:
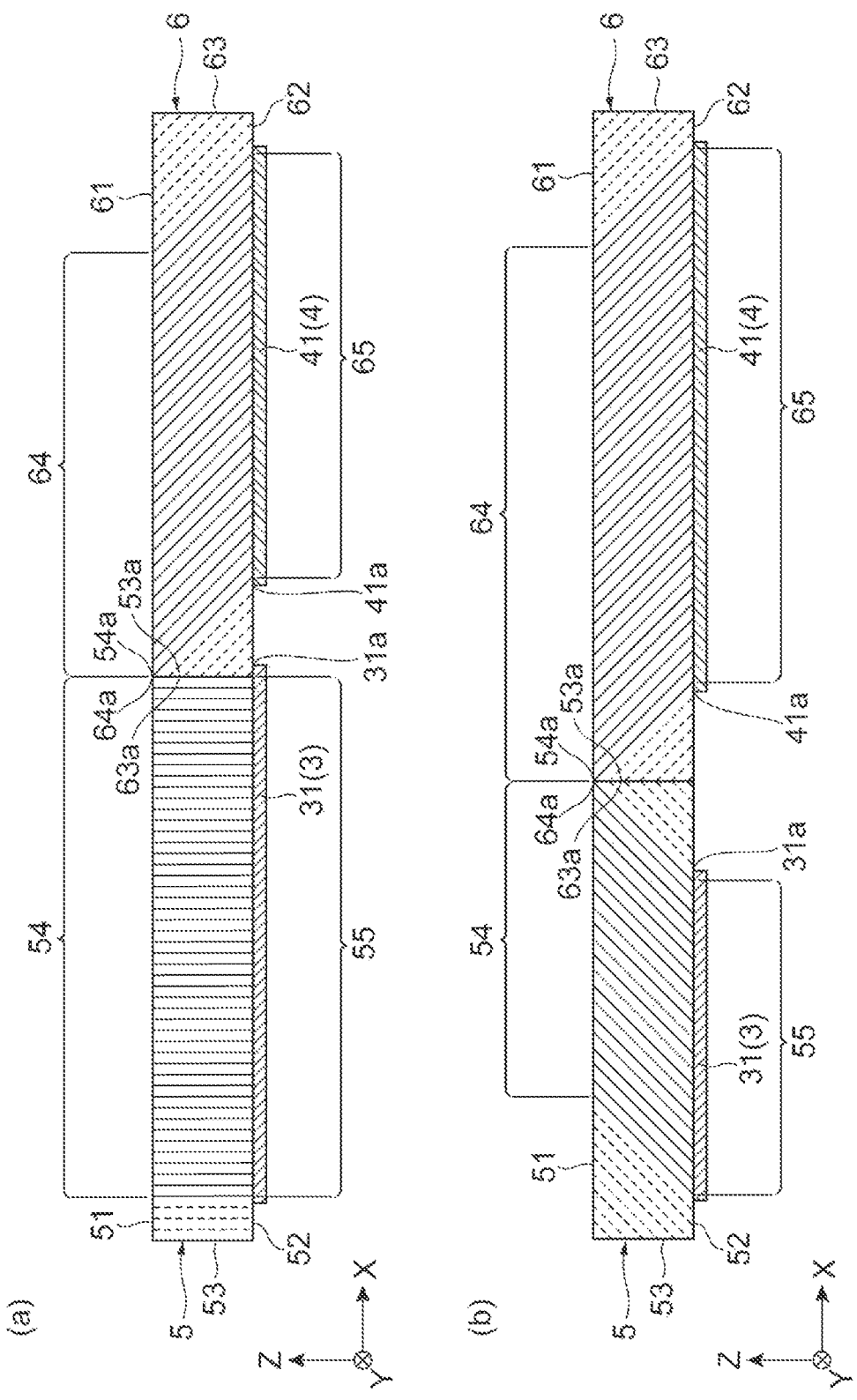
FIG. 11 is a view for illustrating a modification example of the radiation detector.

In addition, as long as the conditions in which the one side 54*a* of the first light entering region 54 and the one side 64*a* of the second light entering region 64 are in contact (line contact) with each other and the one side surface 53*a* of the first side surface 53 and the one side surface 63*a* of the second side surface 63 exhibit shapes along each other and in contact (surface contact) with each other are satisfied, as shown in (a) of FIG. 11, the plurality of optical fibers constituting the first FOP 5 (or the plurality of optical fibers constituting the second FOP 6) may extend in a direction perpendicular to the first light entering surface 51 and the second light entering surface 61.

In addition, as long as the conditions in which the one side 54*a* of the first light entering region 54 and the one side 64*a* of the second light entering region 64 are in contact (line contact) with each other and the one side surface 53*a* of the first side surface 53 and the one side surface 63*a* of the second side surface 63 exhibit shapes along each other and in contact (surface contact) with each other are satisfied, as shown in (b) of FIG. 11, a length of the first FOP 5 and a length of the second FOP 6 in the X axis direction may differ from each other. In addition, as long as the same conditions are satisfied, as shown in (a) of FIG. 12, a length of the first FOP 5 and a length of the second FOP 6 in the Y axis direction may differ from each other. In addition, as long as the same conditions are satisfied, as shown in (b) of FIG. 12, the first FOP 5 and the second FOP 6 may be disposed in a state of deviating from each other in the Y axis direction.

Figure 13:
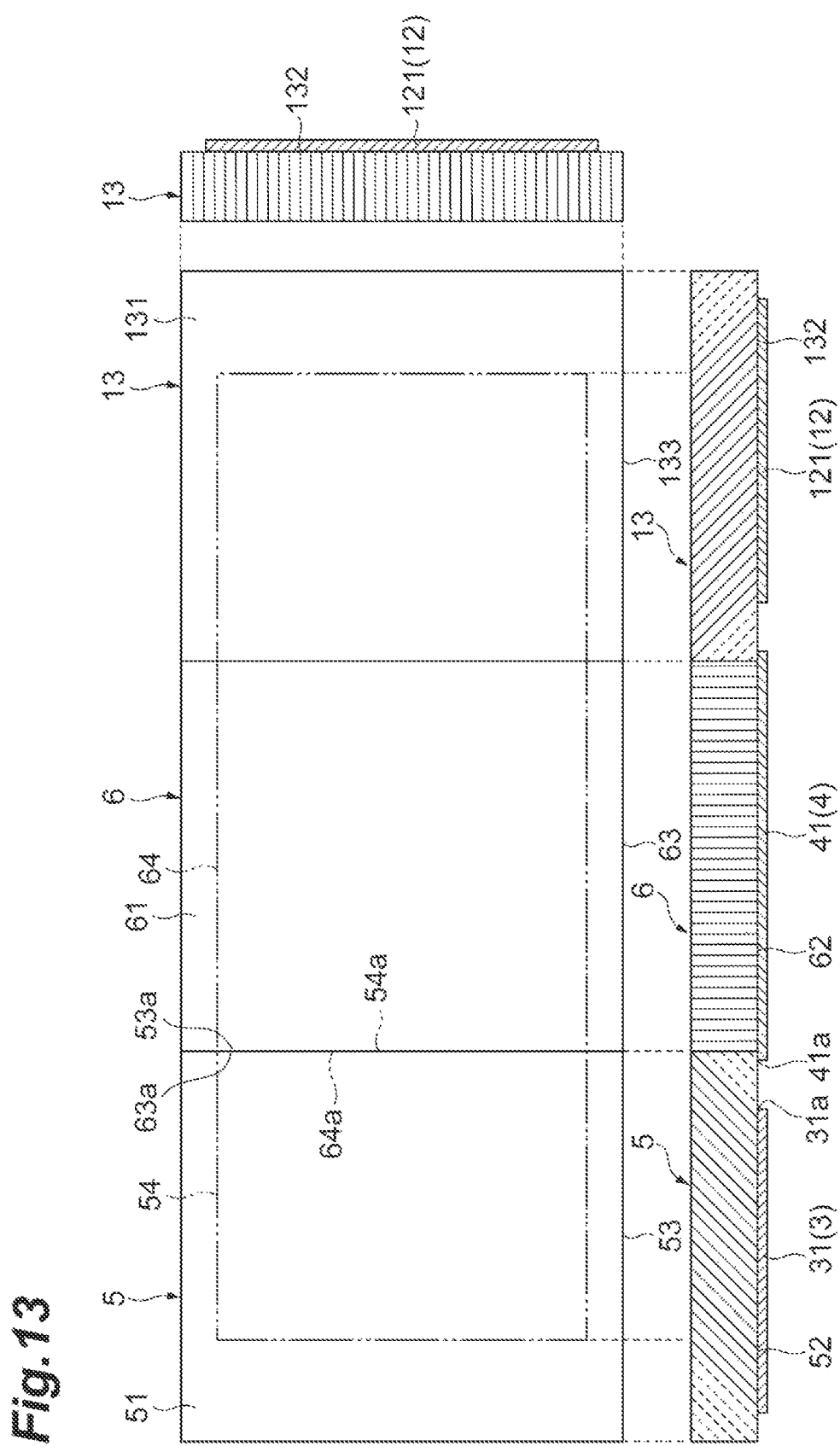
FIG. 13 is another view for illustrating the modification example of the radiation detector.

In addition, as shown in FIG. 13, the radiation detector 1 may further include a third FOP 13 having a third light entering surface 131, a third light exiting surface 132, and a third side surface 133. The first FOP 5, the second FOP 6, and the third FOP 13 may be disposed in series. In the constitution shown in FIG. 13, FOPs adjacent to each other satisfy conditions in which one side of one light entering region on the other light entering region side and one side of the other light entering region on the one light entering region side are in contact (line contact) with each other and one side surface of a side surface of one FOP on the other FOP side and one side surface of a side surface of the other FOP on the one FOP side exhibit shapes along each other and in contact (surface contact) with each other. The third FOP 13 is provided on a third image sensor 12 having a third light receiving region 121. In addition, the plurality of optical fibers constituting the second FOP 6 disposed between the first FOP 5 and the third FOP 13 extend in a direction perpendicular to the second light entering surface 61.

Figure 14:
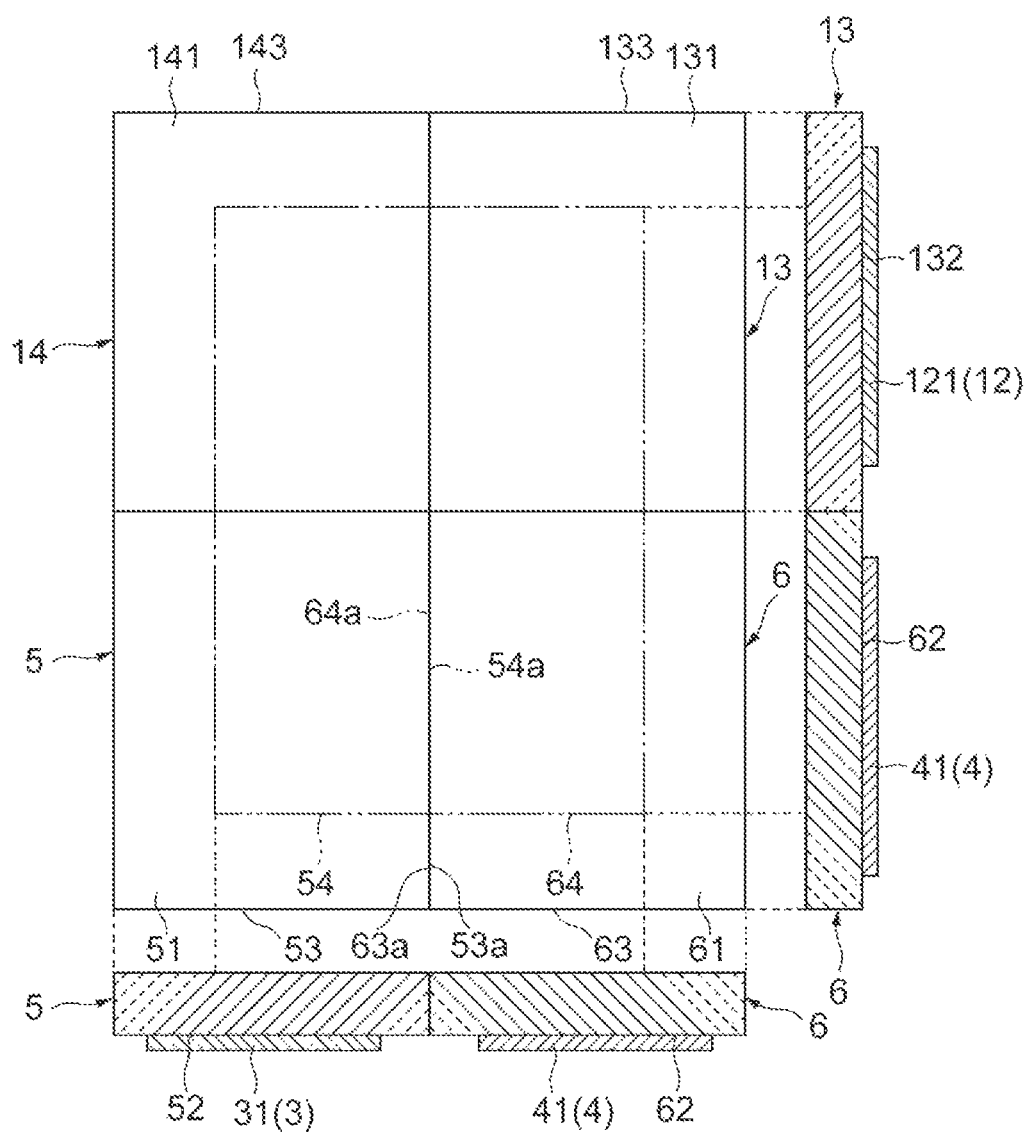
FIG. 14 is another view for illustrating the modification example of the radiation detector.

In addition, as shown in FIG. 14, the radiation detector 1 may further include the third FOP 13 having the third light entering surface 131, the third light exiting surface 132, and the third side surface 133 and a fourth FOP 14 having a fourth light entering surface 141, a third light exiting surface (not shown in the diagram), and a fourth side surface 143. The first FOP 5, the second FOP 6, the third FOP 13, and the fourth FOP 14 may be disposed in a matrix shape. In the constitution shown in FIG. 14, FOPs adjacent to each other satisfy conditions in which one side of one light entering region on the other light entering region side and one side of the other light entering region on the one light entering region side are in contact (line contact) with each other and one side surface of a side surface of one FOP on the other FOP side and one side surface of a side surface of the other FOP on the one FOP side exhibit shapes along each other and in contact (surface contact) with each other. The third FOP 13 is provided on the third image sensor 12 having the third light receiving region 121, and the fourth FOP 14 is provided on a fourth image sensor (not shown in the diagram) having a fourth light receiving region.

In addition, the outer edge E1 of the first light entering surface 51 and the second light entering surface 61 continuous with each other and the outer edge E2 of the first light exiting surface 52 and the second light exiting surface 62 continuous with each other need only include at least the first light receiving region 31 and the second light receiving region 41 when viewed in the Z axis direction. In such a case as well, deterioration due to radiation of at least the first light receiving region 31 and the second light receiving region 41 can be curbed.

In addition, in the method for manufacturing the radiation detector 1, regarding the first FOP 5 and the second FOP 6 bonded to each other, at least the first light entering surface 51 and the second light entering surface 61 need only be polished. In such a case as well, the scintillator layer 7 can be formed on the first FOP 5 and the second FOP 6 in a state in which the first light entering surface 51 and the second light entering surface 61 are flush with each other, and thus occurrence of a distortion or the like in the scintillator layer 7 can be curbed.

In addition, in the method for manufacturing the radiation detector 1, in the step of bonding, the first FOP 5 and the second FOP 6 may be bonded onto the first image sensor 3 and the second image sensor 4 mounted on the wiring board 2, and thereafter the scintillator layer 7 may be formed on the first FOP 5 and the second FOP 6. In this case, the scintillator layer 7 having a lower strength than other members is formed last. Therefore, occurrence of damage to the scintillator layer 7 can be curbed.

In addition, in the method for manufacturing the radiation detector 1, the first deviation amount and the second deviation amount may not be stored in the storage portion 21 provided on the wiring board 2. In such a case, in the image processing method using the radiation detector 1, for example, the image processing device may acquire the first deviation amount and the second deviation amount (step of acquiring) by reading the first deviation amount and the second deviation amount which have been separately stored in the storage portion, and the image processing device may generate one X-ray transmission image on the basis of the first electrical signal, the second electrical signal, the first deviation amount, and the second deviation amount (step of generating). In addition, in an X-ray transmission image generated without considering the first deviation amount and the second deviation amount, the image processing device may acquire the first deviation amount and the second deviation amount (step of acquiring) by extracting a gap (a region lacking in pixel value) generated between an image based on the first electrical signal and an image based on the second electrical signal on the basis of the pixel value, and the image processing device may generate one X-ray transmission image on the basis of the first electrical signal, the second electrical signal, the first deviation amount, and the second deviation amount (step of generating).

In addition, in the method for manufacturing the radiation detector 1, the scintillator layer 7 may be formed on the first FOP 5 and the second FOP 6, and the first FOP 5 and the second FOP 6 may be bonded onto the first image sensor 3 and the second image sensor 4 mounted on the wiring board 2 (step of forming and bonding). Thereafter, the first deviation amount and the second deviation amount may be measured (step of measuring). Thereafter, the first deviation amount and the second deviation amount may be stored in the storage portion 21 provided on the wiring board 2 (step of storing). In such a case, it is not essential to prepare the first FOP 5 and the second FOP 6 bonded to each other in advance and polish the first light entering surface 51 of the first FOP 5 and the second light entering surface 61 of the second FOP 6.

The following methods can be realized for "a radiation detector (which will be referred to as "a radiation detector of another form") including a wiring board, a first image sensor and a second image sensor adjacent to each other on the wiring board, a first fiber optic plate and a second fiber optic plate adjacent to each other on the first image sensor and the second image sensor, and a scintillator layer provided on the first fiber optic plate and the second fiber optic plate. The first fiber optic plate has a first light entering surface, a first light exiting surface, and a first side surface connecting the first light entering surface and the second light exiting surface and is capable of guiding light between a first light entering region of the first light entering surface and a first light exiting region of the first light exiting surface. The second fiber optic plate has a second light entering surface, a second light exiting surface, and a second side surface connecting the second light entering surface and the second light exiting surface and is capable of guiding light between a second light entering region of the second light entering surface and a second light exiting region of the second light exiting surface. One side of the first light entering region on the second light entering region side and one side of the second light entering region on the first light entering region side are in contact with each other. The first light exiting region is positioned on a first light receiving region of the first image sensor. The second light exiting region is positioned on a second light receiving region of the second image sensor".

That is, there is provided a radiation detector manufacturing method of another form. "The radiation detector manufacturing method includes a step of forming the scintillator layer on the first fiber optic plate and the second fiber optic plate and bonding the first fiber optic plate and the second fiber optic plate onto the first image sensor and the second image sensor mounted on the wiring board, a step of measuring the first deviation amount and the second deviation amount after the step of forming and bonding, and a step of storing the first deviation amount and the second deviation amount in the storage portion provided on the wiring board after the step of measuring".

According to this radiation detector manufacturing method of another form, unique first and second deviation amounts are stored in the storage portion in an individual radiation detector. Therefore, a radiation detector capable of accurately generating one radiographic image on the basis of the stored first and second deviation amounts can be manufactured.

In addition, there is provided an image processing method of another form using the radiation detector of another form. "The image processing method includes a step of acquiring a first deviation amount between the one side of the first light exiting region on the second light exiting region side and the one side of the first light receiving region on the second light receiving region side and a second deviation amount between the one side of the second light exiting region on the first light exiting region side and the one side of the second light receiving region on the first light receiving region side, and a step of generating one radiographic image on the basis of a first electrical signal output from the first image sensor via the wiring board, a second electrical signal output from the second image sensor via the wiring board, the first deviation amount, and the second deviation amount after the step of acquiring".

According to this image processing method of another form, unique first and second deviation amounts are acquired in an individual radiation detector. Therefore, one radiographic image can be accurately generated on the basis of the acquired first and second deviation amounts.

REFERENCE SIGNS LIST

1: radiation detector, 2: wiring board, 3: first image sensor, 4: second image sensor, 5: first FOP (first fiber optic plate), 6: second FOP (second fiber optic plate), 7: scintillator layer, 21: storage portion, 31: first light receiving region, 31a: one side, 32, 33: first circuit region, 41: second light receiving region, 41a: one side, 42, 43: second circuit region, 51: first light entering surface, 52: first light exiting surface, 53: first side surface, 53a: one side surface, 54: first light entering region, 54a: one side, 55: first light exiting region, 55a: one side, 61: second light entering surface, 62: second light exiting surface, 63: second side surface, 63a: one side surface, 64: second light entering region, 64a: one side, 65: second light exiting region, 65a: one side.

The invention claimed is:

1. A radiation detector comprising:
a wiring board;
a first image sensor and a second image sensor adjacent to each other on the wiring board;
a first fiber optic plate comprising a plurality of optical fibers and a second fiber optic plate comprising a plurality of optical fibers adjacent to each other on the first image sensor and the second image sensor; and
a scintillator layer provided on the first fiber optic plate and the second fiber optic plate,
wherein the first fiber optic plate has a first light entering surface and a first light exiting surface, and is capable of guiding light between a first light entering region of the first light entering surface and a first light exiting region of the first light exiting surface,
wherein the second fiber optic plate has a second light entering surface and a second light exiting surface, and is capable of guiding light between a second light entering region of the second light entering surface and a second light exiting region of the second light exiting surface,
wherein one side of the first light entering region on a side of the second light entering region and one side of the second light entering region on a side of the first light entering region are in contact with each other,
wherein at least a part of one side of the first light exiting surface on a side of the second light exiting surface and at least a part of one side of the second light exiting surface on a side of the first light exiting surface are in contact with each other,
wherein the first light exiting region is positioned on a first light receiving region of the first image sensor,
wherein the second light exiting region is positioned on a second light receiving region of the second image sensor,
wherein the first light entering surface and the first light exiting surface are in a positional relationship of facing each other, and the second light entering surface and the second light exiting surface are in a positional relationship of facing each other, and
wherein a direction along which each of the plurality of optical fibers constituting the first fiber optic plate extends and a direction along which each of the plurality of optical fibers constituting the second fiber optic plate extends are in a positional relationship of intersecting each other.

2. The radiation detector according to claim 1,
wherein a distance between one side of the first light exiting region on a side of the second light exiting region and one side of the second light exiting region on a side of the first light exiting region is longer than a distance between one side of the first light receiving region on a side of the second light receiving region and one side of the second light receiving region on a side of the first light receiving region,
wherein the one side of the first light exiting region on the side of the second light exiting region is positioned on the one side of the first light receiving region on the side of the second light receiving region or on a side inward from the one side of the first light receiving region on the side of the second light receiving region, and
wherein the one side of the second light exiting region on the side of the first light exiting region is positioned on the one side of the second light receiving region on the side of the first light receiving region or on a the side inward from the one side of the second light receiving region on the side of the first light receiving region.

3. The radiation detector according to claim 2, further comprising:
a storage portion provided on the wiring board,
wherein the storage portion stores a first deviation amount between the one side of the first light exiting region on the side of the second light exiting region and the one side of the first light receiving region on the side of the second light receiving region and a second deviation amount between the one side of the second light exiting region on the side of the first light exiting region and the one side of the second light receiving region on the side of the first light receiving region.

4. The radiation detector according to claim 1,
wherein an outer edge of the first light entering surface and an outer edge of the second light entering surface are continuous with each other, and the outer edge of the first light entering surface and the outer edge of the second light entering surface include the first light exiting region and the second light exiting region when viewed in a thickness direction of the wiring board.

5. The radiation detector according to claim 1,
wherein an outer edge of the first light entering surface and an outer edge of the second light entering surface are continuous with each other, and the outer edge of the first light entering surface and the outer edge of the second light entering surface include the first light receiving region and the second light receiving region when viewed in a thickness direction of the wiring board, and
wherein an outer edge of the first light exiting surface and an outer edge of the second light exiting surface are continuous with each other, and the outer edge of the first light exiting surface and the outer edge of the second light exiting surface include the first light receiving region and the second light receiving region when viewed in the thickness direction of the wiring board.

6. The radiation detector according to claim 5,
wherein the first image sensor includes a first circuit region adjacent to the first light receiving region,
wherein the second image sensor includes a second circuit region adjacent to the second light receiving region, and
wherein the outer edge of the first light entering surface, the outer edge of the second light entering surface, the outer edge of the first light exiting surface, and the outer edge of the second light exiting surface include the first light receiving region, the first circuit region, the second light receiving region, and the second circuit region when viewed in the thickness direction of the wiring board.

7. The radiation detector according to claim 1,
wherein each of the plurality of optical fibers constituting the first fiber optic plate extends in a direction perpendicular to the first light entering surface.

8. The radiation detector according to claim 1,
wherein each of the plurality of optical fibers constituting the first fiber optic plate is inclined with respect to a direction perpendicular to the first light entering surface, and
wherein each of the plurality of optical fibers constituting the second fiber optic plate is inclined with respect to a direction perpendicular to the second light entering surface.

9. The radiation detector according to claim 1,
wherein the entire one side of the first light exiting surface on a side of the second light exiting surface and the entire one side of the second light exiting surface on a side of the first light exiting surface are in contact with each other.

10. A method for manufacturing the radiation detector according to claim 1, the method comprising:
a step of acquiring the first fiber optic plate and the second fiber optic plate bonded to each other;
a step of polishing the first light entering surface of the first fiber optic plate and the second light entering surface of the second fiber optic plate after the step of acquiring; and
a step of forming the scintillator layer on the first fiber optic plate and the second fiber optic plate, and bonding the first fiber optic plate and the second fiber optic plate onto the first image sensor and the second image sensor mounted on the wiring board after the step of polishing.

11. The method for manufacturing the radiation detector according to claim 10,
wherein the step of bonding the first fiber optic plate and the second fiber optic plate onto the first image sensor and the second image sensor mounted on the wiring board is performed after the step of forming the scintillator layer on the first fiber optic plate and the second fiber optic plate.

12. The method for manufacturing the radiation detector according to claim 11,
wherein the scintillator layer comprises CsI.

13. The method for manufacturing the radiation detector according to claim 10,
wherein the step of forming the scintillator layer on the first fiber optic plate and the second fiber optic plate is performed after the step of bonding the first fiber optic plate and the second fiber optic plate onto the first image sensor and the second image sensor mounted on the wiring board.

14. The method for manufacturing the radiation detector according to claim 10,
wherein the step of polishing the first light entering surface of the first fiber optic plate and the second light entering surface of the second fiber optic plate includes polishing the first light exiting surface of the first fiber optic plate and the second light exiting surface of the second fiber optic plate.

15. A method for manufacturing the radiation detector according to claim 3, the method comprising:
a step of forming the scintillator layer on the first fiber optic plate and the second fiber optic plate, and bonding the first fiber optic plate and the second fiber optic plate onto the first image sensor and the second image sensor mounted on the wiring board;
a step of measuring the first deviation amount and the second deviation amount after the step of forming and bonding; and
a step of storing the first deviation amount and the second deviation amount in the storage portion provided on the wiring board after the step of measuring.

16. An image processing method using the radiation detector according to claim 2, the image processing method comprising:
a step of acquiring a first deviation amount between the one side of the first light exiting region on the side of the second light exiting region and the one side of the first light receiving region on the side of the second light receiving region and a second deviation amount between the one side of the second light exiting region on the side of the first light exiting region and the one side of the second light receiving region on the side of the first light receiving region; and
a step of generating one radiographic image on a basis of a first electrical signal output from the first image sensor via the wiring board, a second electrical signal output from the second image sensor via the wiring board, the first deviation amount, and the second deviation amount after the step of acquiring.

* * * * *